United States Patent
Guo

(10) Patent No.: US 11,452,983 B2
(45) Date of Patent: Sep. 27, 2022

(54) COMBINATION OF ISOLATED INDIVIDUAL ENHANCEMENTS OF X-RAY RADIATION EFFECT BY NANOMATERIALS

(71) Applicant: The Regents of the University of California, Oakland, CA (US)

(72) Inventor: Ting Guo, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 786 days.

(21) Appl. No.: 15/826,869

(22) Filed: Nov. 30, 2017

(65) Prior Publication Data

US 2018/0085731 A1 Mar. 29, 2018

Related U.S. Application Data

(63) Continuation of application No. PCT/US2016/035502, filed on Jun. 2, 2016.
(Continued)

(51) Int. Cl.
*B01J 19/12* (2006.01)
*A61N 5/10* (2006.01)
(Continued)

(52) U.S. Cl.
CPC .......... *B01J 19/125* (2013.01); *A61N 5/00* (2013.01); *A61N 5/10* (2013.01); *B01J 21/08* (2013.01);
(Continued)

(58) Field of Classification Search
CPC ........ B01J 31/0271; B01J 23/52; B01J 21/08; B01J 35/0006; B01J 35/0013; B01J 2219/0877; B01J 2219/0892; B01J 35/003; B01J 2219/1203; B01J 19/125; A61N 5/00; A61N 2005/1098; A61N 5/10; B82Y 40/00; A61P 43/00; A61P 35/00;
(Continued)

(56) References Cited

U.S. PATENT DOCUMENTS 9,604,955 B2 * 3/2017 Guo .................. C07D 311/12
2008/0003183 A1 * 1/2008 Guo .................. A61K 41/0038
977/810
(Continued)

FOREIGN PATENT DOCUMENTS

WO 2015031675 3/2015
WO 2016196783 12/2016

OTHER PUBLICATIONS

Park et al, "Cooperative Nanomaterial System to Sensitize, Target, and Treat Tumors," Proceedings of the National Academy of Sciences of the United States of America, vol. 107, No. 3 (Jan. 19, 2010), pp. 981-986 (Year: 2010).*
(Continued)

*Primary Examiner* — Xiuyu Tai
(74) *Attorney, Agent, or Firm* — Kilpatrick Townsend & Stockton LLP

(57) ABSTRACT

The present disclosure relates to methods of combining chemical enhancement and physical enhancement to produce a combined synergistic total enhancement, and more specifically to methods of irradiating samples containing nanomaterials capable of producing chemical or physical enhancement to produce combined synergistic total enhancement.

23 Claims, 10 Drawing Sheets

Related U.S. Application Data

(60) Provisional application No. 62/191,214, filed on Jul. 10, 2015, provisional application No. 62/171,169, filed on Jun. 4, 2015.

(51) Int. Cl.

| | | |
|---|---|---|
| *B01J 35/00* | (2006.01) | |
| *B01J 21/08* | (2006.01) | |
| *B01J 23/52* | (2006.01) | |
| *A61N 5/00* | (2006.01) | |
| *B82Y 40/00* | (2011.01) | |
| *B01J 31/02* | (2006.01) | |

(52) U.S. Cl.
CPC ........... *B01J 23/52* (2013.01); *B01J 31/0271* (2013.01); *B01J 35/0006* (2013.01); *B01J 35/0013* (2013.01); *A61N 2005/1098* (2013.01); *B01J 2219/0877* (2013.01); *B01J 2219/0892* (2013.01); *B01J 2219/1203* (2013.01); *B82Y 40/00* (2013.01)

(58) Field of Classification Search
CPC ............ A61K 49/0041; A61K 49/0054; A61K 51/065; A61K 47/6929; A61K 47/6923; A61K 51/1251; A61K 49/0065; C08G 65/3344; C08G 65/33334; C07D 491/18; Y10S 977/777
USPC ....................................... 204/157.44, 157.63
See application file for complete search history.

(56) References Cited

U.S. PATENT DOCUMENTS

| | | | |
|---|---|---|---|
| 2010/0034735 A1 | 2/2010 | Chen et al. | |
| 2010/0140560 A1 | 6/2010 | Wang et al. | |
| 2010/0260676 A1* | 10/2010 | Hanson .................... | B82Y 5/00 424/9.1 |
| 2011/0165647 A1* | 7/2011 | Fernig .................... | B82Y 15/00 977/810 |
| 2011/0230760 A1* | 9/2011 | Gambhir ................ | B82Y 15/00 600/431 |
| 2014/0186263 A1* | 7/2014 | Schirrmacher ...... | A61K 51/065 |
| 2014/0371471 A1 | 12/2014 | Guo | |
| 2015/0265706 A1* | 9/2015 | Vo-Dinh ................ | A61P 31/00 424/490 |
| 2016/0038111 A1* | 2/2016 | Maidment .......... | A61K 49/0423 600/431 |
| 2016/0067524 A1* | 3/2016 | Bourke, Jr. ............. | B01J 19/12 600/1 |
| 2016/0200872 A1* | 7/2016 | Guo .......................... | C08F 2/44 522/66 |

OTHER PUBLICATIONS

Nanopartz, "Gold Nanorods Properties, Applications, and Products" downloaded from https://www.nanopartz.com/gold_nanorods.asp on Sep. 29, 2019 (Year: 2019).*
Derwent abstract of CN104587485 (Year: 2015).*
Naya et al, "Visible-Light-Induced Electron Transport from Small to Large Nanoparticles in Bimodal Gold Nanoparticle-Loaded Titanium(IV) Oxide," Angew. Chem. Int. Ed. 2014, 53, 7305-7309 DOI: 10.1002/anie.201402939 (Year: 2014).*
Carter et al., Nanoscale Energy Deposition by X-Ray Absorbing Nanostructures, J. Phys. Chem. B, vol. 111, No. 40, Sep. 14, 2007, pp. 11622-11625.
Cheng et al., Chemical Enhancement by Nanomaterials Under X-Ray Irradiation, J. Am. Chem. Soc. Commun., vol. 134, No. 4, Jan. 19, 2012, pp. 1950-1953.
Davidson et al., An Example of X-ray Nanochemistry: SERS Investigation of Polymerization Enhanced by Nanostructures under X-ray Irradiation, Journal of Physical Chemistry Letters, vol. 3, No. 22, Oct. 25, 2012, pp. 3271-3275.
Davidson et al., Average Physical Enhancement by Nanomaterials under X-Ray Irradiation, Journal of Physical Chemistry C, vol. 118, No. 51, Dec. 2, 2014, pp. 30221-30228.
Duff et al., A New Hydrosol of Gold Clusters .2. A Comparison of Some Different Measurement Techniques, Langmuir, vol. 9, No. 9, Sep. 1993, pp. 2310-2317.
Foley et al., Enhanced Relaxation of Nanoparticle-Bound Supercoiled DNA in X-Ray Radiation, Chem. Commun., vol. 25, May 24, 2005, pp. 3192-3194.
Guo et al., Nanoparticle Enhanced X-Ray Therapy, ACS Annual Meeting 2004: Philadelphia, PA, 2004, 1 page.
Hainfeld et al., The Use of Gold Nanoparticles to Enhance Radiotherapy in Mice, Phys. Med. Bio, vol. 49, No. 18, 2004, pp. N309-N315.
Ionita et al., Dual Behavior of Gold Nanoparticles, as Generators and Scavengers for Free Radicals, Journal of Materials Science, vol. 43, Issue 19, Oct. 2008, pp. 6571-6574.
Kimling et al., Turkevich Method for Gold Nanoparticle Synthesis Revisited, Journal of Physical Chemistry B, vol. 110, No. 32, Jul. 21, 2006, pp. 15700-15707.
Lee et al., Geometry Enhancement of Nanoscale Energy Deposition by X-Rays, J. Phys. Chem. C, vol. 116, No. 20, Apr. 11, Apr. 11, 2012, pp. 11292-11297.
Olszanski et al., The IRS Fricke Dosimetry System, Aug. 2002, 69 pages.
International Application No. PCT/US2016/035502, International Preliminary Report on Patentability dated Dec. 14, 2017, 6 pages.
International Application No. PCT/US2016/035502, International Search Report and Written Opinion dated Sep. 7, 2016, 8 pages.
Perrault et al., Synthesis and Surface Modification of Highly Monodispersed, Spherical Gold Nanoparticles of 50-200 nm, Journal of the American Chemical Society, vol. 131, No. 47, Nov. 5, 2009, pp. 17042-17043.
Schunemann, Mesoporous Silica Supported Au and AuCu Nanoparticles for Surface Plasmon Driven Glycerol Oxidation, Chem. Mater., vol. 27, No. 22, Oct. 27, 2015, pp. 7743-7750.

* cited by examiner

COMBINATION OF ISOLATED INDIVIDUAL ENHANCEMENTS OF X-RAY RADIATION EFFECT BY NANOMATERIALS

CROSS-REFERENCES TO RELATED APPLICATIONS

The present application is a continuation of International Patent Application No. PCT/US2016/035502 filed Jun. 2, 2016, which claims the benefit of and priority to U.S. Provisional Application Nos. 62/171,169, filed Jun. 4, 2015, and 62/191,214, filed on Jul. 10, 2015, which applications are herein incorporated by reference in their entirety for all purposes.

STATEMENT REGARDING FEDERALLY-SPONSORED RESEARCH

This invention was made with government support under Grant No. CHE-1307529 awarded by the National Science Foundation. The government has certain rights in the invention.

FIELD

The present technology relates to methods of combining chemical enhancement and physical enhancement to produce a combined synergistic total enhancement. More specifically, the present technology relates to methods of irradiating samples containing nanomaterials capable of producing chemical or physical enhancement to produce combined synergistic total enhancement.

BACKGROUND

The work of using nanomaterials to enhance the effect of X-rays began more than a decade ago.[1-3] The origins of enhancement come from at least two main sources: (1) the increased absorption of X-rays that in turn causes an increased release of electrons from nanomaterials and (2) catalytic functionality of nanoparticles enabled by X-ray generated species such as OH radicals in solution.[4-6] Unless special care is given to isolating and maximizing these individual sources, they co-exist, interfere, and convolute in most experiments to create a total enhancement, which can be divided into several categories including physical, chemical, anti-, and possibly biological enhancement. Each category of enhancement can be further separated into many types. For instance, physical enhancement (PE) can be separated into at least two types, types 1 and 2. Type 1 PE (T1PE) represents the average or remote physical enhancement, whereas type 2 PE (T2PE) describes the local or nanoscale physical enhancement.[7,8] Unlike PE, chemical enhancement (CE) is reaction dependent and does not require the nanoparticles to absorb X-rays much more than the surrounding water.[5] However, CE does need the nanoparticles to be catalytically active when they interact with X-ray generated species in solution. In addition, many nanomaterials naturally scavenge radicals and these nanomaterials act as anti-enhancement chemical reagents.[9] When these individual enhancements are arbitrarily combined, the total enhancement produced is generally much lower than the highest possible enhancement a nanomaterial or several of them may potentially offer. This problem can be corrected if these individual enhancements are properly identified, isolated, optimized, and then combined to achieve a much higher total enhancement. The total enhancement obtained after the isolation-optimization-combination process may depend on the individual enhancements through different algorithms such as addition, subtraction, or multiplication.

Recent efforts have been given to investigating individual enhancement, and some of the above-mentioned enhancements have been isolated. For example, T1PE has been studied experimentally.[7] CE can be isolated by using small nanoparticles that do not generate significant PE, and several CE reactions have been identified. One example of CE is polymerization of aniline enabled by OH radical oxidation of metal nanostructures.[6] Another example is superoxide-caused catalytic conversion of intermediates.[5] Despite these efforts, there has been no attempt to combine these individually identified enhancements to create a much higher total enhancement. Thus, there exists a need to develop methods of beneficially and synergistically combining the individual effects of physical and chemical enhancements to produce a higher total enhancement.

BRIEF SUMMARY

In one aspect, the present disclosure relates to a method of enhancing a chemical reaction, the method including: a) providing a sample including: (1) a first population of nanomaterials including (i) an active metal surface, and (ii) a diameter in the range of 1 nm to 10 nm; (2) a second population of nanomaterials including a diameter in the range of 10 nm to 1,000 nm; (3) one or more chemical reactants; and, b) irradiating the sample with irradiation energy for a period of time sufficient for the one or more chemical reactants to undergo a chemical reaction to yield one or more products, where the chemical reaction occurs at a reaction rate that is increased as compared to a corresponding control sample. In some embodiments, the sample includes water. In some embodiments that may be combined with any of the preceding embodiments, the first population of nanomaterials includes nanoparticles. In some embodiments, the nanoparticles include gold (Au). In some embodiments that may be combined with any of the preceding embodiments, the first population of nanomaterials include a ligand including tetrakis (hydroxymethyl) phosphonium chloride (THPC). In some embodiments that may be combined with any of the preceding embodiments, the first population of nanomaterials is present in the sample at a concentration in the range of about 0.001 to about 0.1 weight percent first population of nanomaterials in the sample.

In some embodiments that may be combined with any of the preceding embodiments, the first population of nanomaterials include a diameter in the range of 1 nm to 5 nm. In some embodiments that may be combined with any of the preceding embodiments, the first population of nanomaterials are present about 1 nm to about 10 nm away from the one or more chemical reactants. In some embodiments that may be combined with any of the preceding embodiments, the second population of nanomaterials includes nanoparticles. In some embodiments, the nanoparticles include gold (Au). In some embodiments that may be combined with any of the preceding embodiments, the second population of nanomaterials include a ligand including silica. In some embodiments that may be combined with any of the preceding embodiments, the second population of nanomaterials is present in the sample at a concentration in the range of about 0.1 to about 10 weight percent second population of nanomaterials in the sample. In some embodiments that may be combined with any of the preceding embodiments, the second population of nanomaterials includes a diameter in the range of 10 nm to 200 nm. In some embodiments that may be combined with any of the preceding embodiments, the second population of nanomaterials are present about 0.1 µm to about 10 µm away from the one or more chemical reactants. In some embodiments that may be combined with any of the preceding embodiments, the second population of nanomaterials includes an inert surface.

In some embodiments that may be combined with any of the preceding embodiments, the irradiation energy includes X-rays. In some embodiments that may be combined with any of the preceding embodiments, the irradiation energy is filtered. In some embodiments that may be combined with any of the preceding embodiments, the irradiation energy comes from multiple sources. In some embodiments that may be combined with any of the preceding embodiments, the X-ray irradiation is at a dose rate in the range of about 0.01 Gy/min to about 100 Gy/min. In some embodiments that may be combined with any of the preceding embodiments, the corresponding control sample is a sample which does not include the first population of nanomaterials and/or the second population of nanomaterials.

The present technology also includes a nanomaterial mixture including a first population of nanomaterials and a second population of nanomaterials. The first population of nanomaterials may be characterized by an active metal surface and a diameter in the range of 1 nm to 10 nm. For example, the diameter may be between about 1 nm and 5 nm, or between about 1 nm and 3 nm. Additionally, the first population of nanomaterials may be present in the sample at a concentration in the range of about 0.01 to about 0.1 weight percent first population of nanomaterials in the nanomaterial mixture, or any of the other weight percentages discussed elsewhere in this disclosure.

The second population of nanomaterials may be characterized by a diameter in the range of 10 nm to 1,000 nm. For example, the diameter may be in the range of about 10 nm and about 100 nm, about 50 nm and about 200 nm, or between about 90 nm and about 500 nm. The second population of nanomaterials may be present in the sample at a concentration in the range of about 1 to about 10 weight percent second population of nanomaterials in the nanomaterial mixture. In embodiments the nanomaterial mixture may also include, or may not include, one or more chemical reactants.

When combined with chemical reactants, the first population of nanomaterials and the second population of nanomaterials of the nanomaterial mixture may be configured to cause the chemical reactants to undergo a chemical reaction to yield one or more products when irradiated with irradiation energy for a period of time. The nanomaterials may cause the chemical reaction to occur at a reaction rate that is increased as compared to a corresponding control sample. The irradiation energy utilized may be between about 1.0 Gy/min and about 30 Gy/min in embodiments. For example, the irradiation energy may be up to about 3.0 Gy/min. When irradiated, the nanomaterial mixture may cause an increase in the deposition of energy from the irradiation energy when compared to the deposition of energy from the irradiation energy in a corresponding control sample. For example, in embodiments the nanomaterial mixture may cause at least a 5-fold increase, at least a 10-fold increase, at least an 18-fold increase, at least a 50-fold increase, or at least a 100-fold increase in the deposition of energy from the irradiation energy when compared to the deposition of energy from the irradiation energy in the corresponding control sample. A chemical enhancement to the reaction rate may also occur in combination with a physical enhancement, and may cause at least a 2-fold increase to the reaction rate as compared to a corresponding control sample, at least a 10-fold increase to the reaction rate, at least a 30-fold increase to the reaction rate, and at least a 100-fold increase to the reaction rate as compared to a corresponding control sample in embodiments.

where a=3, b=5, and x is the effective dose rate.

Figure 9:
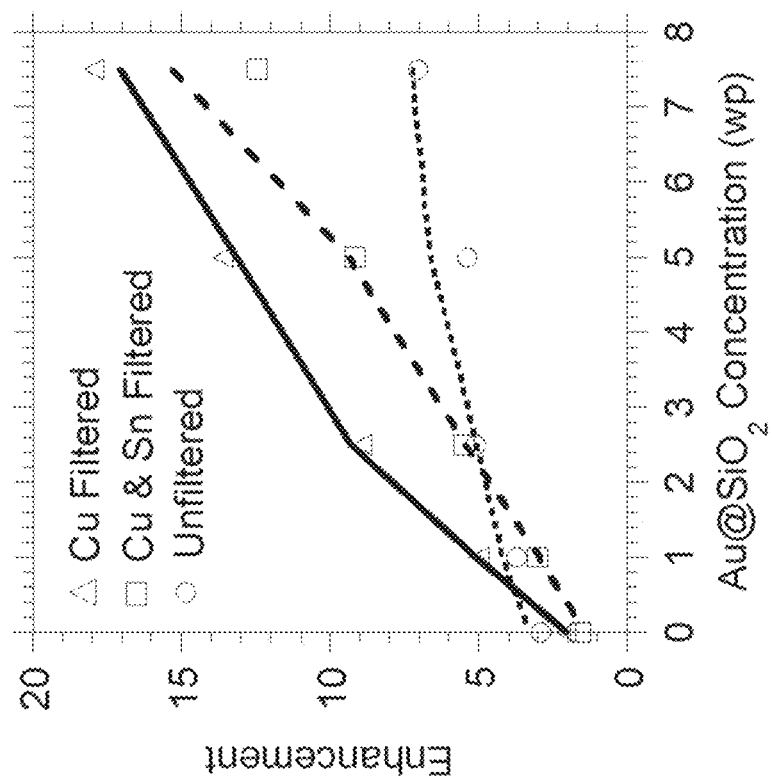

FIG. 9 illustrates the simulated enhancement (relative) using rate equations to model chemical enhancement described previously.[5] All rate constants were kept the same as before except the constant responsible for chemical enhancement was changed for each X-ray spectral case. General agreements exist between experimental and simulation results. Saturation is observed for higher dose rate cases including both unfiltered and one Cu filter case. The simulation shows a slight quadratic trend for the lowest dose rate range associated with the double Cu/Sn filter case.

Figure 10:
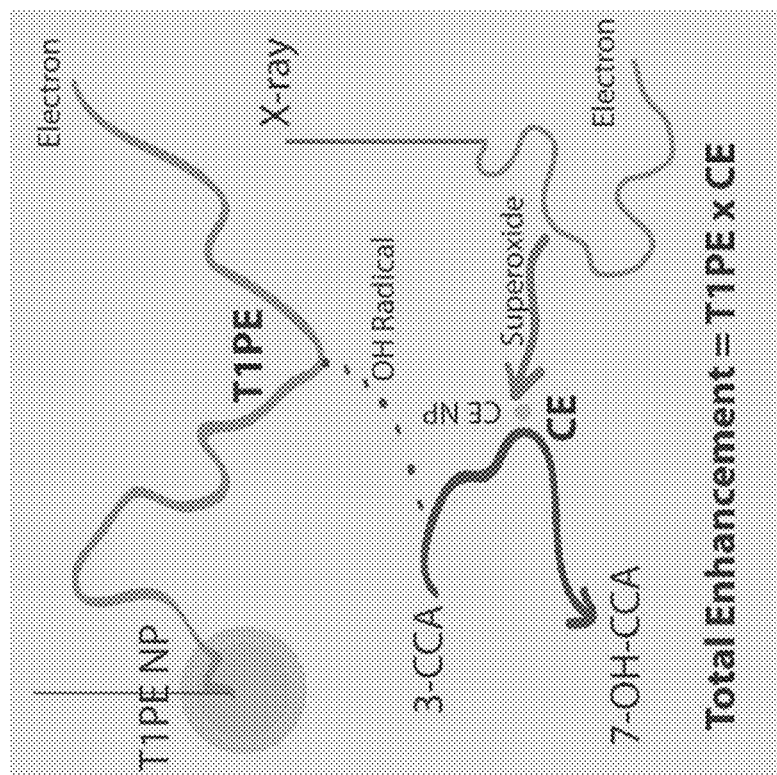

FIG. 10 illustrates the depiction of total enhancement as the multiplication of type 1 physical enhancement and chemical enhancement.

DETAILED DESCRIPTION

The following description is presented to enable a person of ordinary skill in the art to make and use the various embodiments. Descriptions of specific devices, techniques, and applications are provided only as examples. Various modifications to the examples described herein will be readily apparent to those of ordinary skill in the art, and the general principles defined herein may be applied to other examples and applications without departing from the spirit and scope of the various embodiments. Thus, the various embodiments are not intended to be limited to the examples described herein and shown, but are to be accorded the scope consistent with the claims.

Introduction

The present disclosure relates to methods of combining chemical enhancement and physical enhancement to produce a combined synergistic total enhancement, and more specifically to methods of irradiating samples containing nanomaterials capable of producing chemical or physical enhancement to produce combined synergistic total enhancement.

The present disclosure is based, at least in part, on Applicant's discovery of how to combine individual enhancement mechanisms (e.g. physical and chemical enhancement) of X-ray effects by nanomaterials to, surprisingly, create a much stronger total enhancement. Only recently have these individual enhancement mechanisms been isolated and measured. However, there was no record on how to use them collectively or whether there is any advantage of using them together. Here it is shown for the first time that there are surprising and significant benefits for combining these individual enhancement mechanisms to achieve a much stronger total enhancement. An example is shown in which one enhancement of type 1 physical enhancement (T1PE) of 5.5 fold is combined with another enhancement of net chemical enhancement (CE0) of 2.0 fold (measured without the presence of T1PE causing nanomaterials) to generate a total enhancement of 18.0 fold by using the same two nanomaterials in a mixture. Applicants found that the total enhancement follows a multiplication algorithm between the experimentally determined T1PE and CE. CE in this example is different from CE0 and is a function of CE0 and the dose rate, which may be controlled by T1PE and other parameters.

Overall, the methods and compositions described herein allow one to achieve a surprisingly high total enhancement that is unattainable through other methods of using only one kind or type of enhancement mechanism. Further, fewer/lower concentrations of nanomaterials may be used to achieve the same total enhancement that would arise using only one of chemical or physical enhancement. Furthermore, the methods and compositions described herein allow one to arrange nanomaterials at different locations such as, for example, places inaccessible to large T1PE nanoparticles, such as in the cell nuclei where only small, less than 20 nm nanoparticles may enter. The present disclosure also opens the door for using multiple X-ray sources with different X-ray energy spectra to maximize T1PE and CE separately and then together the total enhancement can be much greater.

Definitions

Unless specifically indicated otherwise, all technical and scientific terms used herein have the same meaning as commonly understood by those of ordinary skill in the art to which this technology belongs. In addition, any method or material similar or equivalent to a method or material described herein can be used in the practice of the present technology. For purposes of the present technology, the following terms and phrases are defined.

The terms "a," "an," or "the" as used herein not only include aspects with one member, but also include aspects with more than one member. For instance, the singular forms "a," "an," and "the" include plural referents unless the context clearly dictates otherwise.

"Active metal surface" may refer to a surface of a nanomaterial that is catalytically active. For example, the surface may be at least partially free of ligands or other connected materials to maintain surface catalytic activity. By being catalytically active, the metal surface may increase the rate of a chemical reaction, such as for chemical reactants included in a solution with nanomaterials of the present technology, while the metal surface may not be consumed or undergo any permanent chemical change.

"Chemical Enhancement" or "CE" may refer to further catalytic modifications by nanomaterials in addition to physical enhancements. Chemical enhancement may utilize reactive oxygen species generated in a surrounding medium, such as water, for example, and thus to cause chemical enhancement, the nanomaterials may absorb X-rays less strongly than the absorption to produce physical enhancement.

"Chemical Reactants" may refer to one or more chemical species that are utilized or activated, or changed by reaction in the disclosed methods. The reactants may be activated by the nanomaterials to cause a rate of reaction of the chemical reactants to increase. Chemical reactants may include any materials involved in a chemical reaction where the reaction rate may be increased by chemical or physical enhancement with the nanomaterials of the present disclosure.

An "inert" surface may refer to properties or characteristics of nanomaterials for producing physical enhancement where the surface does not have catalytic activity. For example, the nanomaterials may have a shell or coating that reduces or prevents surface activity of the nanomaterial. The inert surface may be a coating applied about a nanomaterial, such as a silica coating as discussed below in the Example section.

"Type 1 Physical Enhancement" or "T1PE" may refer to released photoelectrons from an absorbing material on a nanoparticle after absorption of primary X-ray photons. The released photoelectrons may be energetic enough to travel micrometers or tens of micrometers in a surrounding media, such as water, for example.

"Type 2 Physical Enhancement" or "T2PE" may refer to released low-energy photoelectrons (<5 keV) and secondary electrons generated by absorption of primary X-ray photons. These electrons can generate greater densities of energy deposition about the absorbing materials due to the shorter distances they travel in a surrounding media, such as water, for example.

As used herein, the symbol "@" may identify particles positioned inside of other particles. For example, "A@B"

may identify that particles of "A" are disposed within particles of "B." The particles of "B" may be positioned or coupled as a shell about the particles of "A", and may be a complete or incomplete shell in embodiments.

Samples

Nanomaterials may be used to enhance the effects of irradiation energy when such energy comes into contact with a sample or comes into contact with a target in a sample. As described above, these enhancements of the effects of irradiation energy contacting nanomaterials may be divided into e.g. chemical enhancements and physical enhancements. Various samples (e.g. solutions, subjects, etc.), which may contain one or more targets, may be used in which these enhancement effects occur according to the methods of the present disclosure, as will be readily understood by one of skill in the art.

In some embodiments, a sample of the present disclosure is or includes a solution or mixture. Solutions of the present disclosure may be aqueous solutions that include, for example, water. In such solutions, water may be the only aqueous component of the solution, or the solution may contain other solvents and/or solutes. Solutions may also be smaller or more specific volumes or areas within a larger body or mass (e.g. a subject). For example, when the subject is a human, the solution may be a region of the human's blood stream. One of skill in the art will readily recognize additional types of solutions that may be used in the methods described herein.

In some embodiments, a sample of the present disclosure is or includes a subject. Subjects of the present disclosure may be bodies or masses that may be subjected to the methods described herein. For example, a subject may be a living system such as a living cell, cell culture, tissue, organ, or organism. In some embodiments, the subject is a living human or other mammal. One of skill in the art will readily recognize additional types of subjects that may be used in the methods described herein.

Targets of the present disclosure may include e.g. molecules, compositions, etc. that are intended to experience a chemical or physical change as a result of the enhancement effects of irradiation energy in the presence of nanomaterials of the present disclosure. For example, the target may be a chemical reactant that is capable of forming one or more products. In some embodiments, the target may be a DNA or RNA molecule. In some embodiments, the target may be a therapeutic agent. One of skill in the art will readily recognize additional types of targets that may be used in the methods described herein.

Nanomaterials for Chemical Enhancement

The present disclosure relates to methods of producing synergistic effects of irradiation energy on nanomaterials by combining chemical and physical enhancements. Accordingly, disclosed herein are nanomaterials that are capable of producing chemical enhancement. The nanomaterials may be composed, at least in part, of an organic material, an inorganic material, or a combination of an organic material and an inorganic material. In some embodiments, the nanomaterials are nanoparticles. The nanoparticle may be a metal-based nanoparticle where the nanoparticle is composed, at least in part, of a metal.

Certain features of the present disclosure relate to nanomaterials capable of producing chemical enhancement that contain a metal surface. The metal surface may cover the entire surface of the nanomaterial, or the metal surface may cover a portion of the nanomaterial. Suitable metals may include, for example, gold, platinum, osmium, iridium, rhenium, tungsten, silver, hafnium, rhodium, ruthenium, palladium, cobalt, nickel, iron, copper, and rare-earth metals.

Nanomaterials of the present disclosure that are capable of producing chemical enhancement generally contain an active surface (e.g. the metal surface of the nanomaterial is catalytically active). Nanomaterials for chemical enhancement may include one or more ligands attached to the nanomaterial. Generally, such ligands should have properties that allow the nanomaterial to be water soluble, as well as lack a charge that would hinder radical or radical intermediates from approaching the metal surface of the nanomaterials. By way of example, carboxylic acids, such as citrate, are charged molecules that scavenge radicals (e.g. superoxide) and are therefore not suitable for supporting chemical enhancement. Ligands having charged functional groups that react with intermediates may render the metal surface of nanomaterials less catalytically active and are therefore not suitable for supporting chemical enhancement. In some embodiments, even when a nanomaterial for chemical enhancement has attached, at its surface, one or more ligands, at least a portion of the surface of the nanomaterial remains exposed (e.g. not attached to a ligand or the attached ligand still permits access to the nanomaterial surface) such that this surface may remain catalytically active.

Ligands that may be attached to a nanomaterial for chemical enhancement may include, for example, alcohols (—OH) such as THPC (Tetrakis(hydroxymethyl)phosphonium chloride), ethers and poly ethers (—O—) such as polyethylene glycol (PEG) and thiolated PEG, pyridines such as pyridine octanethiols, amines such as thiol-PEG-$NH_2$ (deprotonated amines), and anilines or ketones. Ligands for chemical enhancement may be charged ligands as long as there is only one charged functional group and it is attached to the metal surface of the nanomaterial, leaving the rest in solvent. One such example is a thiol ligand. Although a thiol ligand is commonly used at pH 7 and is in the deprotonated form (anion), it is still possible to use this type of ligand if the thiol end is linked to the metal surface of the nanomaterial and therefore cannot interfere with enhancing the reaction to be catalyzed.

Nanomaterials for use in chemical enhancement may have a variety of sizes. In some embodiments, the nanomaterial is about 1 nm to about 100 nm in diameter. In some embodiments, the nanomaterial is about 0.5 nm to about 30 nm in diameter. The diameter of the nanomaterial may be, for example, about 1 nm to about 5 nm, about 5 nm to about 10 nm, about 10 nm to about 15 nm, about 15 nm to about 20 nm, about 20 nm to about 25 nm, about 25 nm to about 30 nm, about 30 nm to about 35 nm, about 35 nm to about 40 nm, about 40 nm to about 45 nm, about 45 nm to about 50 nm, about 50 to about 75 nm, or about 75 nm to about 100 nm. The diameter of the nanomaterial may be, for example, about 1 nm to about 10 nm, about 10 nm to about 20 nm, about 20 nm to about 30 nm, about 30 nm to about 40 nm, about 40 nm to about 50 nm, or about 50 nm to about 100 nm. The diameter of the nanomaterial may be, for example, about 1 nm to about 15 nm, about 15 nm to about 30 nm, about 30 nm to about 50 nm, or about 50 nm or more in diameter. The diameter of the nanomaterial may be, for example, about 1 nm to about 3 nm, about 3 nm to about 5 nm, about 5 nm to about 7 nm, or about 7 nm to about 10 nm. The diameter of the nanomaterial may be, for example, about 1 nm to about 7 nm, about 1 nm to about 9 nm, about 1 nm to about 20 nm, about 1 nm to about 30 nm, about 1 nm to about 40 nm, or about 1 nm to about 50 nm or more in diameter. The diameter of the nanomaterial may be, for example, about 0.5 nm, about 1 nm, about 2 nm, about 3 nm, about 4 nm, about 5 nm, about 6 nm, about 7 nm, about 8 nm, about 9 nm, about 10 nm, about 11 nm, about 12 nm, about 13 nm, about 14 nm, about 15 nm, about 16 nm, about 17 nm, about 18 nm, about 19 nm, about 20 nm, about 21 nm, about 22 nm, about 23 nm, about 24 nm, about 25 nm, about 26 nm, about 27 nm, about 28 nm, about 29 nm, about 30 nm, about 31 nm, about 32 nm, about 33 nm, about 34 nm, about 35 nm, about 36 nm, about 37 nm, about 38 nm, about 39 nm, about 40 nm, about 41 nm, about 42 nm, about 43 nm, about 44 nm, about 45 nm, about 46 nm, about 47 nm, about 48 nm, about 49 nm, or about 50 nm or more in diameter. Generally speaking, for chemical enhancement, smaller size nanomaterials will generate a more profound enhancement due to the high surface-to-volume ratio for a fixed amount of nanomaterials.

For chemical enhancement, the concentration of nanomaterials in a sample may vary. In some embodiments, the concentration of nanomaterials in the sample is in the range of about 0.001 to about 0.1 weight percent of nanomaterials in sample. For example, the concentration of nanomaterials in the sample may be in the range of about 0.001 to about 0.005, about 0.005 to about 0.01, about 0.01 to about 0.05, about 0.05 to about 0.1, about 0.1 to about 0.2, about 0.2 to about 0.3, about 0.3 to about 0.4, about 0.4 to about 0.5, about 0.5 to about 0.6, about 0.6 to about 0.7, about 0.7 to about 0.8, or about 0.8 to about 0.9 weight percent of nanomaterials in sample. The concentration of nanomaterials in the sample may be, for example, in the range of about 0.001 to about 0.01, about 0.01 to about 0.1, or about 0.1 to about 0.9 weight percent of nanomaterials in sample. The concentration of nanomaterials in the sample may be, for example, in the range of about 0.005 to about 0.01, about 0.01 to about 0.5, or about 0.5 to about 0.9 weight percent of nanomaterials in sample. The concentration of nanomaterials in the sample may be, for example, about 0.001 to about 0.05, about 0.001 to about 0.5, or about 0.001 to about 0.9 weight percent of nanomaterials in sample. The concentration of nanomaterials in the sample may be, for example, about 0.001, about 0.002, about 0.003, about 0.004, about 0.005, about 0.006, about 0.007, about 0.008, about 0.009, about 0.01, about 0.02, about 0.03, about 0.04, about 0.05, about 0.06, about 0.07, about 0.08, about 0.09, about 0.1, about 0.2, about 0.3, about 0.4, about 0.5, about 0.6, about 0.7, about 0.8, or about 0.9 weight percent of nanomaterials in sample.

Nanomaterials for Physical Enhancement

The present disclosure relates to methods of producing synergistic effects of irradiation energy on nanomaterials by combining chemical and physical enhancements. Accordingly, disclosed herein are nanomaterials that are capable of producing physical enhancement. The nanomaterials may be composed, at least in part, of an organic material, an inorganic material, or a combination of an organic material and an inorganic material (e.g. a combination of more than one organic material and more than one inorganic material). In some embodiments, the nanomaterials are nanoparticles. The nanoparticle may be a metal-based nanoparticle where the nanoparticle is composed, at least in part, of a metal.

Certain features of the present disclosure relate to nanomaterials capable of producing physical enhancement that contain e.g. a metal surface, semiconductor surface, or insulator surface. One or more (e.g. a mixture) of these surfaces may cover the entire surface of the nanomaterial or a portion thereof. Suitable metals may include, for example, gold, platinum, titanium, tungsten, silver, and rare-earth metals. Suitable semiconductor surfaces may include, for example, GaAs, PbS, Si, Ge, $Cu_2O$, and CdSe. Suitable insulator surfaces may include, for example, $SiO_2$, ZnO, $Al_2O_3$, $TiO_2$, and oxides of rare earth metals.

Nanomaterials of the present disclosure that are capable of producing physical enhancement may contain an inert surface (e.g. at least a portion of the surface of the nanomaterial is catalytically inert) or they may contain an active surface (e.g. at least a portion of the surface of the nanomaterial is catalytically active). Generally, a nanomaterial that is outside the target or chemical reactant does not require an inert surface, whereas a nanomaterial that is near the target or chemical reactant will have an inert surface. A wide variety of nanomaterials may be used for physical enhancement, regardless of surface. Generally speaking, less active or inert surface nanomaterials may produce greater physical enhancement. Further, and generally speaking, the thinner the surface coverage of a nanomaterial for physical enhancement, whether it is a layer of inorganic materials such as silica or an organic ligand layer such as PEG, the greater the type 1 physical enhancement due to weaker attenuation of electrons leaving the nanomaterials that cause type 1 physical enhancement.

Nanomaterials for physical enhancement may include one or more ligands attached to the surface of the nanomaterial. Generally, nanomaterials for physical enhancement that contain a surface which does not permit solubility in a given sample may include one or more ligands attached to the surface to promote solubility in the given sample. To provide an example of nanomaterials that will not need additional such ligands to promote solubility, nanomaterials having an insulator surface including e.g. silica ($SiO_2$ or silicon dioxide) generally do not need any additional attached ligands to promote solubility in e.g. water.

Generally speaking, any ligands or surface layer or coating on nanomaterials for type 1 physical enhancement should not hinder the effective release of electrons. The release (or lack thereof) of electrons may be a function of various factors including e.g. the density and thickness of the surface layer (e.g. the surface and any attached ligands). To prevent the release of electrons, the density of the surface layer may be e.g. between 1.0 $g/cm^3$ and 20 $g/cm^3$, and preferably 1.0 $g/cm^3$ and 5 $g/cm^3$. The thickness of the layer may be e.g. less than 500 nm and preferably less than 50 nm. An example of such a layer is 20 nm thick silica of density of 2.3 $g/cm^3$. Another example of such a layer is 2000 mw PEG, density of 1.2 $g/cm^3$ and less than 10 nm thick measured from the surface of the nanomaterial to the exterior of the PEG layer.

Ligands that may be attached to a nanomaterial for physical enhancement may include, for example, alcohols (—OH) such as THPC (Tetrakis(hydroxymethyl)phosphonium chloride), ethers and poly ethers (—O—) such as polyethylene glycol (PEG) and thiolated PEG, pyridines such as pyridine octanethiols, amines such as thiol-PEG-$NH_2$ (deprotonated amines), and anilines or ketones. Ligands for physical enhancement may be charged ligands as long as there is only one charged functional group and it is attached to the surface of the nanomaterial, leaving the rest in solvent. These ligands are preferred if physical enhancement nanomaterials are within 1-1,000 nm of the target. One such example is a thiol ligand. Although a thiol ligand is commonly used at pH 7 and is in the deprotonated form (anion), it is still possible to use this type of ligand if the thiol end is linked to the surface of the nanomaterial. When the nanomaterials for physical enhancement are 10 nm to 100 nm away from the target, other ligands such as citrate and cetyl trimethylammonium bromide (CTAB)

ligands with multiple charged functional groups per ligand may be used. Generally speaking, when a nanomaterial for type 1 physical enhancement is greater than 10 nm in distance from a target, then charged ligands and various other types of ligands may be used.

For nanomaterials capable of generating physical enhancement, following irradiation with irradiation energy, energy deposition is generally enhanced in the region adjacent to the nanomaterial. The enhancement in the deposition may include an increase in the deposition of energy that is, for example, a 2-fold increase, a 4-fold increase, a 6-fold increase, an 8-fold increase, a 10-fold increase, a 15-fold increase, a 20-fold increase, a 30-fold increase, a 40-fold increase, a 50-fold increase, a 60-fold increase, a 70-fold increase, an 80-fold increase, a 90-fold increase, a 100-fold increase, a 120-fold increase, or a 150-fold or more increase in the deposition of energy from irradiation energy when compared to the deposition of energy from the irradiation energy in the background solution or a corresponding control sample.

Nanomaterials for use in physical enhancement may have a variety of sizes. In some embodiments, the nanomaterial is about 10 nm to about 1,000 nm in diameter or about 11 nm to about 1,000 nm in diameter. The diameter of the nanomaterial may be, for example, about 10 nm to about 50 nm, about 50 nm to about 100 nm, about 100 nm to about 150 nm, about 150 nm to about 200 nm, about 250 nm to about 300 nm, about 300 nm to about 350 nm, about 350 nm to about 400 nm, about 400 nm to about 450 nm, about 450 nm to about 500 nm, about 500 nm to about 550 nm, about 550 nm to about 600 nm, about 600 nm to about 650 nm, about 650 nm to about 700 nm, about 700 nm to about 750 nm, about 750 nm to about 800 nm, about 800 nm to about 850 nm, about 850 nm to about 900 nm, about 900 nm to about 950 nm, or about 950 nm to about 1,000 nm. The diameter of the nanomaterial may be, for example, about 10 nm to about 200 nm, about 100 nm to about 200 nm, about 200 nm to about 400 nm, about 300 nm to about 500 nm, about 500 nm to about 700 nm, or about 700 nm to about 1,000 nm. The diameter of the nanomaterial may be, for example, about 10 nm to about 30 nm, about 30 nm to about 50 nm, about 50 nm to about 75 nm, about 75 nm to about 100 nm, about 100 nm to about 125 nm, about 125 nm to about 150 nm, about 150 nm to about 175 nm, about 175 nm to about 200 nm, or about 200 nm to about 225 nm. The diameter of the nanomaterial may be, for example, about 50 nm to about 150 nm, about 50 nm to about 200 nm, about 50 nm to about 225 nm, about 50 nm to about 250 nm, about 50 nm to about 300 nm, about 100 nm to about 400 nm, about 100 nm to about 500 nm, about 100 nm to about 600 nm, about 100 nm to about 700 nm, about 100 nm to about 800 nm, about 100 nm to about 900 nm, or about 100 nm to about 1,000 nm. The diameter of the nanomaterial may be, for example, about 10 nm, about 11 nm, about 15 nm, about 20 nm, about 25 nm, about 30 nm, about 35 nm, about 40 nm, about 45 nm, about 50 nm, about 55 nm, about 60 nm, about 65 nm, about 70 nm, about 75 nm, about 80 nm, about 85 nm, about 90 nm, about 100 nm, about 110 nm, about 120 nm, about 130 nm, about 140 nm, about 150 nm, about 160 nm, about 170 nm, about 180 nm, about 190 nm, about 200 nm, about 210 nm, about 220 nm, about 230 nm, about 240 nm, about 250 nm, about 260 nm, about 270 nm, about 280 nm, about 290 nm, or about 300 nm or more in diameter.

For physical enhancement, the concentration of nanomaterials in a sample may vary. In some embodiments, the concentration of nanomaterials in the sample is in the range of about 1 to about 10 weight percent of nanomaterials in sample. The concentration of nanomaterials in the sample may be, for example, in the range of about 1 to about 1.5, about 1.5 to about 2, about 2 to about 2.5, about 2.5 to about 3, about 3 to about 3.5, about 3.5 to about 4, about 4 to about 4.5, about 4.5 to about 5, about 5 to about 5.5, about 5.5 to about 6, about 6 to about 6.5, about 6.5 to about 7, about 7 to about 7.5, about 7.5 to about 8, about 8 to about 8.5, about 8.5 to about 9, about 9 to about 9.5, or about 9.5 to about 10 weight percent of nanomaterials in sample. The concentration of nanomaterials in the sample may be, for example, in the range of about 1 to about 3, about 1 to about 5, about 1 to about 7, or about 1 to about 9 weight percent of nanomaterials in sample. The concentration of nanomaterials in the sample may be, for example, in the range of about 2 to about 4, about 4 to about 6, about 6 to about 8, or about 8 to about 10 weight percent of nanomaterials in sample. The concentration of nanomaterials in the sample may be, for example, about 1, about 1.2, about 1.4, about 1.6, about 1.8, about 2, about 2.2, about 2.4, about 2.6, about 2.8, about 3, about 3.2, about 3.4, about 3.6, about 3.8, about 4, about 4.2, about 4.4, about 4.6, about 4.8, about 5, about 5.2, about 5.4, about 5.6, about 5.8, about 6, about 6.2, about 6.4, about 6.6, about 6.8, about 7, about 7.2, about 7.4, about 7.6, about 7.8, about 8, about 8.2, about 8.4, about 8.6, about 8.8, about 9, about 9.2, about 9.4, about 9.6, about 9.8, or about 10 weight percent of nanomaterials in sample.

Irradiation Energy

Certain aspects of the present disclosure relate to the use of irradiation energy. Irradiation energy as described herein may be used in methods of combining chemical and physical enhancements to achieve an overall synergistic enhancement of the effect of irradiation energy on nanomaterials. For example, a nanomaterial-containing sample of the present disclosure may be irradiated with irradiation energy for a period of time sufficient for the one or more chemical reactants to undergo a chemical reaction to yield one or more products.

Various types of irradiation energy may be used according to the methods of the present disclosure. For example, the irradiation may be X-rays. Other ionizing radiation may be used such as, for example, high energy electrons, MeV gamma rays, and X-rays from various sources including accelerator-based laser produced monochromatic X-rays. The source of X-rays may also be a commercial microfocus X-ray source.

Various doses of irradiation energy may be used in the methods described herein. The irradiation energy dose may be at least about 0.1 Gy/min, at least about 0.5 Gy/min, at least about 1 Gy/min, at least about 2 Gy/min, at least about 3 Gy/min, at least about 4 Gy/min, at least about 5 Gy/min, at least about 6 Gy/min, at least about 7 Gy/min, at least about 8 Gy/min, at least about 9 Gy/min, at least about 10 Gy/min, at least about 11 Gy/min, at least about 12 Gy/min, at least about 13 Gy/min, at least about 14 Gy/min, at least about 15 Gy/min, at least about 16 Gy/min, at least about 17 Gy/min, at least about 18 Gy/min, at least about 19 Gy/min, at least about 20 Gy/min, at least about 21 Gy/min, at least about 22 Gy/min, at least about 23 Gy/min, at least about 24 Gy/min, at least about 25 Gy/min, at least about 50 Gy/min, at least about 75 Gy/min, or at least about 100 Gy/min. The irradiation may be at a dose rate in the range of about 0.1 Gy/min to about 100 Gy/min, about 0.1 Gy/min to about 10 Gy/min, about 10 Gy/min to about 50 Gy/min, about 50 Gy/min to about 75 Gy/min, or about 75 Gy/min to about 100 Gy/min.

Exposure of sample to irradiation energy according to the methods of the present disclosure may occur for various times which may vary according to e.g. the dose rate of the irradiation energy. In some embodiments, a sample is irradiated with irradiation energy for a time period in the range of 30 seconds to 1 hour. The time period for irradiating a sample with irradiation energy may be, for example, about 1 minute to about 5 minutes, about 5 minutes to about 10 minutes, about 10 minutes to about 20 minutes, about 20 minutes to about 30 minutes, about 30 minutes to about 40 minutes, about 40 minutes to about 50 minutes, or about 50 minutes to 1 hour. One of skill in the art would readily understand additional suitable irradiation dosing and time periods of irradiation in view of the present disclosure.

In some embodiments, irradiation energy used in the methods of the present disclosure is filtered. Irradiation energy may be filtered through, for example, a copper (Cu) filter or a tin (Sn) filter. In some embodiments, irradiation energy used in the methods of the present disclosure originates from multiple sources. For example, if the targets is in a human body, one can use a low energy source in the form of a catheter implant to deliver 10-30 keV X-rays to the sample or target, and another source of X-rays in the form of a microfocus X-ray tube located outside the body to deliver 60-160 keV X-rays to the sample or target. The penetration depth of 10-30 keV X-rays is only a few millimeters, whereas that for 60-160 keV X-rays is several to tens of thousands of centimeters in the human body.

Enhancing Chemical Reactions

Certain aspects of the present disclosure relate to enhancing a chemical reaction. Chemical reactions may be enhanced by combining chemical and physical enhancements to achieve an overall synergistic enhancement of the effect of irradiation energy on nanomaterials according to the methods of the present disclosure.

Chemical reactions as described herein may occur at a reaction rate that is increased as compared to the reaction rate in a corresponding control sample based on the chemical enhancements (CE) previously discussed, which may occur in addition to physical enhancement, as a combination such as discussed throughout the present disclosure, or separately from physical enhancement in disclosed embodiments. In some embodiments, the rate of the chemical reaction is increased in the range of at least a 1.1-fold increase as compared to a corresponding control sample. The enhancement in the reaction rate may be increased by, for example, at least a 1.2-fold increase, a 1.5-fold increase, a 1.8-fold increase, a 2-fold increase, a 4-fold increase, a 6-fold increase, a 8-fold increase, a 10-fold increase, a 12-fold increase, a 15-fold increase, a 20-fold increase, a 25-fold increase, a 30-fold increase, a 35-fold increase, a 40-fold increase, a 45-fold increase, a 50-fold increase, a 55-fold increase, a 60-fold increase, a 65-fold increase, a 70-fold increase, a 75-fold increase, a 80-fold increase, a 85-fold increase, a 90-fold increase, a 95-fold increase, a 100-fold increase, or more as compared to the reaction rate in a correspondint control sample in embodiments. When considered in combination with physical enhancements, as previously discussed, the combined enhancement may be a multiple of the two enhancement numbers, as additionally explained below in the examples. As one non-limiting example, a 30-fold increase in CE with a 7-fold increase in T1PE produces a 210-fold total enhancement. Additionally, a 10-fold increase in CE with a 15-fold increase in T1PE produces a 150-fold total enhancement from CE and T1PE.

Various appropriate corresponding control samples may be used herein, as will be readily apparent to one of skill in the art. For example, the corresponding control sample may be a sample that does not contain nanomaterials capable of generating chemical enhancement, a sample that does not contain nanomaterials capable of generating physical enhancement, a sample that does not contain any nanomaterials capable of generating either chemical or physical enhancement, or a sample that does not contain any nanomaterials at all (e.g. a sample of water).

EXAMPLES

The following examples are offered to illustrate provided embodiments and are not intended to limit the scope of the present disclosure.

Example 1

Multiplication Algorithm for Combined Physical and Chemical Enhancement of X-ray Effect by Nanomaterials This Example demonstrates the synergistic combination of individual physical and chemical enhancements. The total enhancement obtained from mixing (1) silica-covered 90-nm gold nanoparticles and (2) tetrakis (hydroxymethyl) phosphonium-covered 2-nm gold nanoparticles, that individually under X-ray irradiation produced type 1 physical enhancement and chemical enhancement respectively, was studied experimentally and theoretically. The total or combined enhancement was shown to be the multiplication of the two individual enhancements, and this algorithm is derived from the original definition of physical and chemical enhancement. The maximum total enhancement was 18 fold, whereas the maximum measured type 1 physical enhancement was 7 fold and the derived chemical enhancement was 3.9 fold; all three were achieved under different conditions. Simulation results using rate equations for chemical enhancement were obtained and were found to agree with the measured total enhancements.

In this Example, Applicants investigated how T1PE and CE interact with each other. When two or more enhancements are combined, the total enhancement depends on the individual enhancements in a complex way. Since anti-enhancement generally reduces all other enhancements, it should follow a subtraction algorithm between anti-enhancement and other individual enhancements. The enhancements may also reinforce each other. For example, T1PE and CE may interact with each other. Because CE is dose rate dependent and because T1PE is equivalent to increasing the dose rate, the total enhancement should be dependent on both T1PE and CE. Demonstration and verification of these algorithms are critical because if it is a multiplication algorithm for T1PE and CE, then the total enhancement can be much higher than either individually. The highest isolated T1PE reported in the literature was up to 6 fold and the highest CE was 30 fold.[6, 7] If the two enhancements follow a multiplication algorithm, then the total enhancement is greater than 180-fold enhancement, whereas an addition algorithm will give only 35 fold total enhancement. A multiplication algorithm would encourage one not to spend all the effort to maximizing individual enhancements, but instead optimizing the combined total enhancement from moderately high individual enhancements.

In this Example, nanomaterials were chosen that have only T1PE and CE respectively and mixed together to study the combined effect of T1PE and CE. In order to produce T1PE, nanoparticles are needed that have large diameters, low surface areas, and inert surfaces. To create high CE, on the other hand, small diameter, high surface area, and active surface nanoparticles are needed. These two sets of characteristics for the nanomaterials lie at the opposite ends of the parameter space defining nanomaterials and imply that two different kinds of nanomaterials are needed. Furthermore, these two nanomaterials should not interfere with each other with respect to their solubility and stability so that they still maintain their functionalities when mixed. Although it is possible to use just one kind of AuNPs to accomplish both T1PE and CE, it is difficult for a nanoparticle to meet all the requirements.

Specifically, in this Example a chemically inert nanomaterial AuNP@$SiO_2$ to generate T1PE was used, and a chemically active, small tetrakis (hydroxymethyl) phosphonium chloride (THPC)-coated AuNPs to create CE was used. In the work shown here, T1PE is of the order of several fold at the rate of 1 fold per 1 weight percent (wp) of gold in water using AuNP@$SiO_2$, and CE is about 1 to 3 fold with 0.02 wp of gold in water using THPC-AuNPs. It was found that the total enhancement depends on the two enhancements through a multiplication algorithm. The outcome shown here exemplifies the importance of categorizing these enhancements, which enables isolation of individual enhancements so that they can be optimized and recombined to generate a much higher total enhancement.

Experimental and Theoretical Methods

Figure 1:
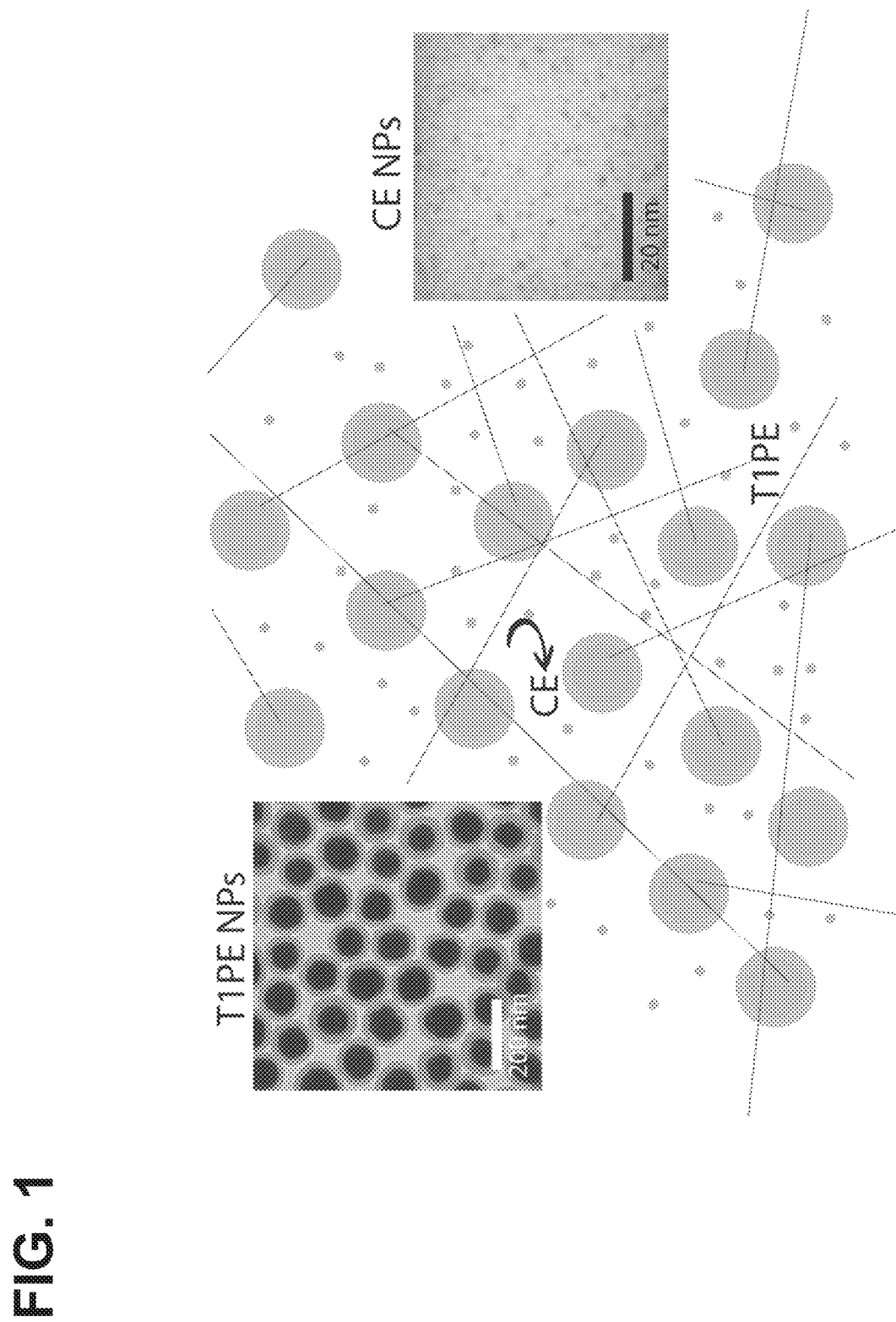
FIG. 1 illustrates how T1PE and CE are generated by AuNP@SiO$_2$ and THPC-AuNPs, respectively. TEM images of AuNP@SiO$_2$ and THPC-AuNPs are also shown in the insets. Lines and arrows are drawn to signify trajectories of electrons released from large AuNPs in silica shells and these electrons are responsible for T1PE. CE is caused by the gold surface of the small THPC-AuNPs.

The overall experimental procedure of combining T1PE from large AuNP@$SiO_2$ and CE from small THPC-AuNPs as well as theoretical simulation using rate equations are described here. Briefly, large gold nanoparticles (AuNPs) in silica shells (AuNP@$SiO_2$) were synthesized using a seed growth method modified from an established method.[10, 11] Small tetrakis (hydroxymethyl) phosphonium chloride (THPC) stabilized AuNPs (THPC-AuNPs) were synthesized using an established method.[12] A microfocus X-ray source with a tungsten target and two sets of filters (Cu filter and Cu+Sn filters) to produce three unique X-ray spectra (including the unfiltered X-ray spectrum) was used in the experiments. The dosimetric reaction of 3-carboxycoumarin acid (3-CCA) to 7-hydroxycoumarin-3-carboxylic acid (7-OH-CCA) was used to measure the enhancement and Fricke dosimeter was used to measure the dose rate associated with the three X-ray spectra. [13] Modeling of the algorithm enhancement using rate laws was carried out using a previously established method.[5] FIG. 1 shows the two nanomaterials separately achieving T1PE and CE, and together, greater total enhancement. The following sections give the details of these experimental and theoretical procedures.

Chemicals 30 wp gold (III) chloride solution in dilute HCl ($HAuCl_4$), hydroquinone, trisodium citrate, polyvinylpyrrolidone (PVP, 40 kD MW), tetraethyl orthosilicate (TEOS), 3-carboycoumarin acid (3-CCA), sodium borohydride ($NaBH_4$), tetrakis (hydroxymethyl) phosphonium chloride (THPC) 80% in water were purchased from Sigma-Aldrich and used as is. Ammonium hydroxide (28 wp), sodium hydroxide pellets (NaOH), dimethyl sulfoxide (DMSO), potassium phosphate dibasic and potassium phosphate monobasic were purchased from Fisher Scientific and used as is. Ethanol 200 proof (Koptec) was obtained from VWR International. Metal foils of 0.127 mm thick Cu (99.9%) and 0.25 mm thick Sn (99.988%) as X-ray filters were obtained from Alfa Aeser and Strem Chemicals Inc., respectively. Milli-Q (MQ) water was used exclusively.

Gold Core-Silica Shell Nanoparticles (AuNP@$SiO_2$)

These particles were made according to a procedure published recently. Briefly, large AuNP cores were synthesized first. They were then coated with PVP ligands and the PVP-coated AuNPs were coated with a layer of silica by reacting with TEOS in the presence of $NH_3OH$. AuNP@$SiO_2$ was concentrated by centrifugation to about 15 wp of gold in water.

2.3 nm THPC Stabilized AuNPs (THPC-AuNPs)

In a beaker, 1 mL 6 M NaOH and 12 µL THPC was added to 45.5 mL MQ water with stirring. Separately, 35 µL of $HAuCl_4$ was added to 1.965 mL of MQ water. Under vigorous stirring, the gold solution was quickly added to the beaker. The solution was allowed to stir for 5 min. after which the beaker was sealed with parafilm and stored in the dark at 4° C. for 24 hours. Dialysis was performed to purify the THPC-AuNPs. FisherBrand dialysis tubing [12 k-14 k MWCO] was used and dialysis water was changed 3 times over a 24 hours period. Once purified, the solution was concentrated approximately 17 fold using centrifugal filtration at 5 k rpm for 8 min. (Amicon Ultra-15 Centrifugal Filter Unit, 30 k MWCO). The concentration was verified by dissolution in aqua regia and measured by AA and the size was measured with TEM to 2.3±0.75 nm.

TEM Imaging

Samples were prepared by drop drying 15 µL of sample on a Lacey carbon grid (Ted Pella Inc.). TEM was performed with a JEOL 1230 operated at 100 kVp.

3-CCA Assay

A 20 mM 3-CCA solution dissolved in 10 mL 80 mM pH 7.4 phosphate buffer (PB) was gently heated and stirred in a sealed flask until dissolution. The solution was then cooled to room temperature and kept protected from light. 7.1 µL DMSO was added to 1 mL of the 3-CCA solution to yield a 20 mM 3-CCA/100 mM DMSO solution.

X-Ray Source and Filters

A microfocus X-ray source with a tungsten target (PXS10-WB-10 mm, Thermo-Kevex) was used in all irradiation experiments. Operation parameters were 400 µA and 120 kVp with Cu and Sn foils as filters: the single filter set consists of 0.127 mm thick Cu and the double filter set 0.127 mm Cu and 0.25 mm Sn to filter the X-ray spectrum. For X-ray irradiation experiments without filters, the operational parameters were 200 µA 120 kVp. The dose rate was measured using Fricke dosimeter according to the IRS protocol (Olszanski-2002).

X-Ray Irradiation Procedure

X-ray irradiation was performed as follows. Four samples were irradiated by X-rays simultaneously according to the parameters stated above. All irradiation times were 20 min. Samples were prepared to contain 5 mM 3-CCA and 25 mM DMSO in 40 µL water. T1PE samples included 0 to 7.5 wp Au@$SiO_2$. Samples for the purpose of combining T1PE and CE included 0.02 wp THPC-AuNPs and 0 to 7.5 wp Au@$SiO_2$. Control samples were spiked after irradiation with predetermined amounts of Au nanomaterials.

Once samples were irradiated, they were diluted to 300 µL with MQ water, vortexed, and centrifuged at 13 k rpm for 10 min. to remove Au nanomaterials. A 100 µL aliquot of supernatant was diluted to 500 µL with 80 mM pH 10 PB. Quantitative fluorometric analysis on the final sample solutions were performed with an excitation wavelength of 395 nm and emission wavelength of 442 nm (FluoroMax-P, HORIBA Jobin Yvon).

Simulation Method

Figure 4:
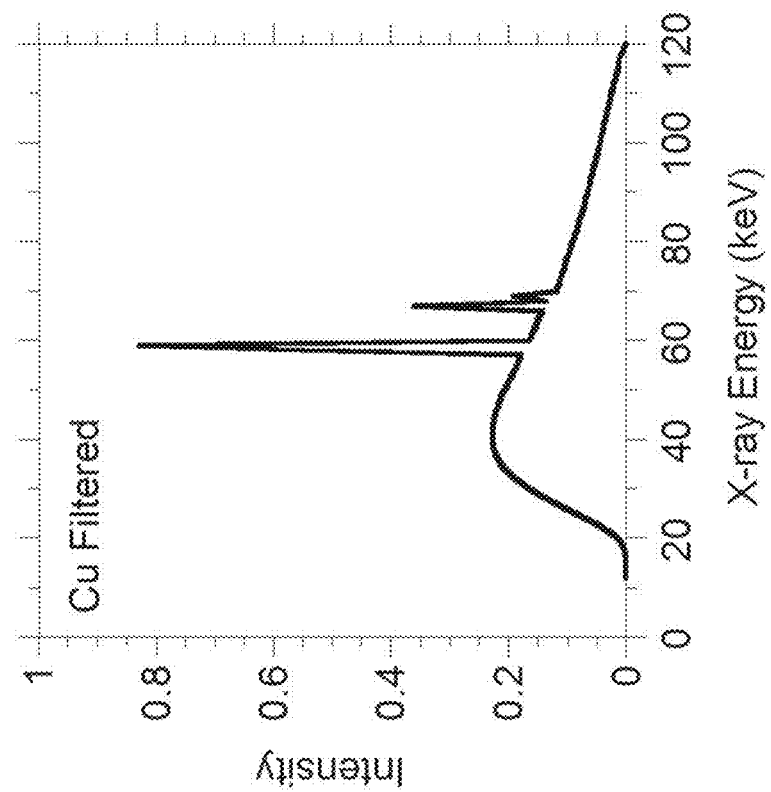
FIG. 4 illustrates the calculated X-ray spectrum filtered with one Cu filter. Peak flux was normalized to the peak flux of the unfiltered spectrum.

Rate law equations were used to model the enhanced production of 7-OH-CCA in the presence of Au nanomaterials. The rate equations were developed previously and modified with the insertion of T1PE from adding AuNP@SiO$_2$.[5] The rate constants used here are given in Table 1 below. All rate equations were identical to those used in a previous publication (Cheng et al.). The only rate constant that was adjusted was that controlling how gold nanoparticles catalyze the conversion from 3-CCA intermediates to the final product 7-OH-CCA. Three rate constant values are given in Table 1 and were used to simulate the results obtained in FIG. 4. The other parameters that were different among three cases are the dose rates without AuNP@SiO$_2$ and the modified dose rates after AuNP@SiO$_2$ were introduced. Experimental values of dose rates measured with Fricke dosimeter without AuNP@SiO$_2$ and experimental values of T1PE were used in the simulation.

TABLE 1

Rate constants for rate equations and enhancement simulation

|  | Rate Constant |
|---|---|
| One filter | $1.4 \times 10^9$ |
| Unfiltered | $4 \times 10^8$ |
| Double filter | $1.4 \times 10^9$ |

Enhancement

Figure 2:
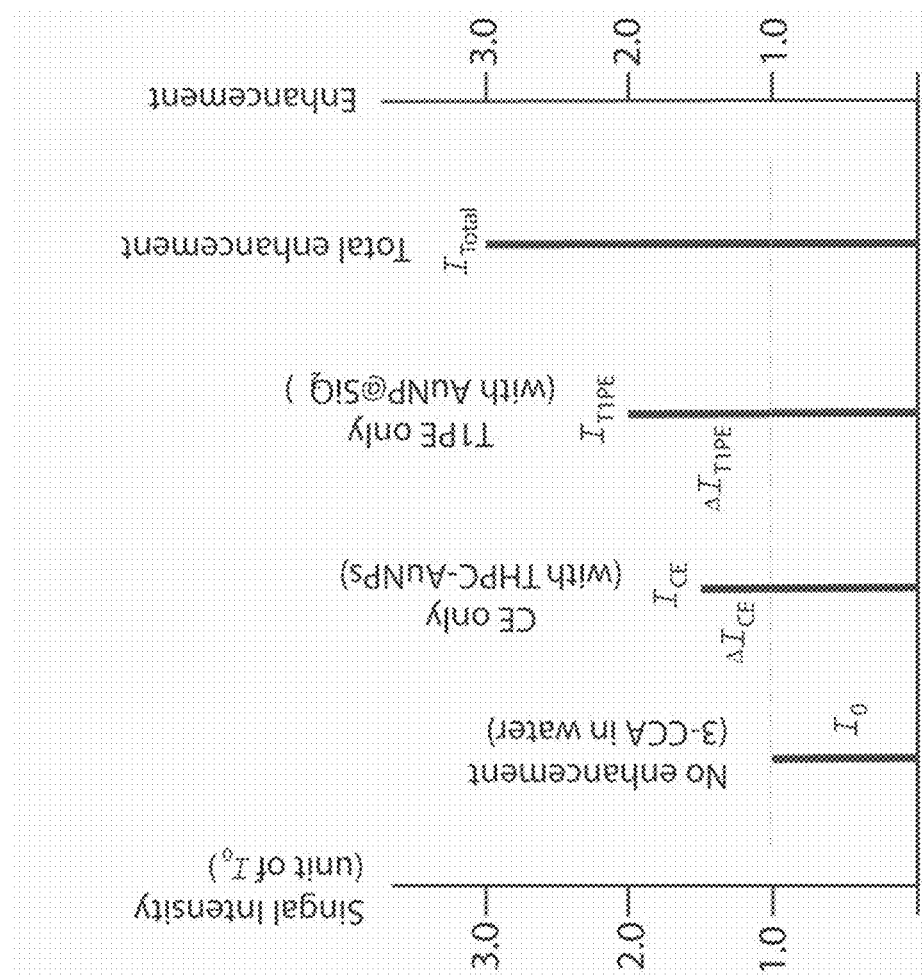
FIG. 2 illustrates descriptions of enhancement. The signals from the probe in pure water, with CE nanoparticles, T1PE nanoparticles, and both CE and T1PE nanoparticles are shown. If the signal from pure water is defined as $I_0$, then the enhancements have the same numerical values as the signal. For instance, if CE is 1.5, then the signal of CE is 1.5 times $I_0$. Both scales are shown.

Enhancement described in this Example refers to the measured fluorescent signal from 7-OH-CCA by nanomaterials compared to that without nanomaterials. Based on this, the enhancement for pure water is 1.0. This is referred to as the relative enhancement. It is also possible to describe an absolute enhancement, which should be zero without nanomaterials. An illustration of how these measured signals and various enhancements are described is given in FIG. 2 in which the fluorescent signal of 7-OH-CCA without nanomaterials is denoted $I_0$. If there is only CE, then the signal is increased to $I_{CE}$. In this Example, relative CE ($\epsilon_{CE}^r$) is the ratio of $I_{CE}$ to $I_0$. The net increase is $\Delta I_{CE}$ and the absolute CE $\epsilon_{CE}^a$ is the ratio of $\Delta I_{CE}$ to $I_0$. Similarly, if there is only T1PE, then the measured signal is $I_{T1PE}$. The net increase is $\Delta I_{T1PE}$. The relative T1PE $\epsilon_{T1PE}^r$ is the ratio of $I_{T1PE}$ to $I_0$, and the absolute T1PE $\epsilon_{T1PE}$ is the ratio of $\Delta I_{T1PE}$ to $I_0$. When both CE and T1PE are present, the total signal is $I_{Total}$, and the total enhancement $\epsilon_{Total}^r$ is the ratio of $I_{Total}$ to $I_0$. If the signal is displayed in the unit of $I_0$, then the enhancement and signal share the same numerical values, as shown in FIG. 2. CE can also be described at a dose rate without AuNP@SiO$_2$ as $\epsilon_{CE0}^r$, which is the net CE and is dose rate dependent.

Results

The nanomaterials used here are shown in FIG. 1, which include THPC-AuNPs for CE and AuNP@SiO$_2$ for T1PE. FIG. 1 shows how these nanomaterials are used, and FIG. 2 illustrates how the enhancement signals are described.

Figure 3:
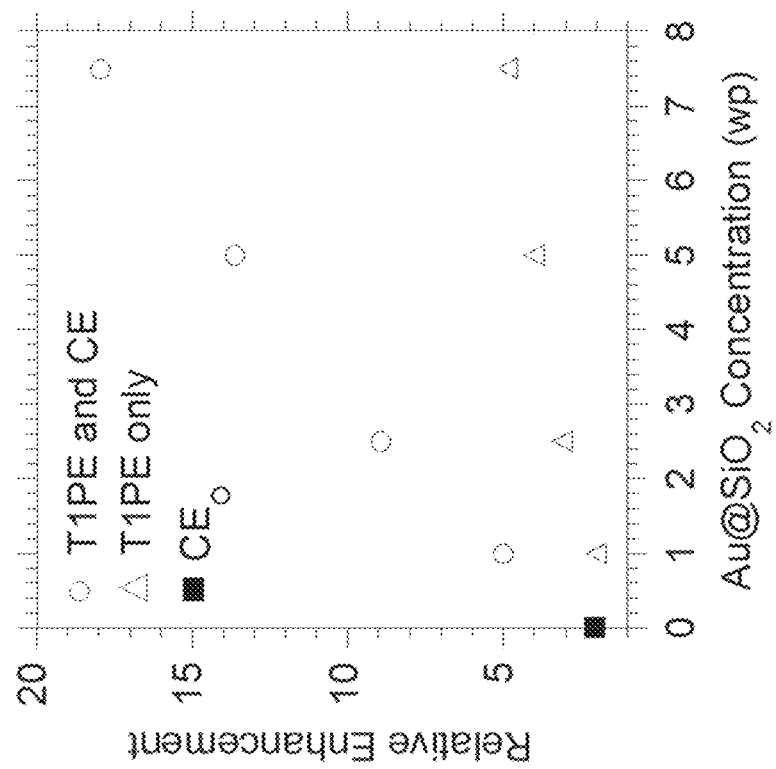
FIG. 3 illustrates the results of enhancement measurement using one Cu filter on the X-ray source. The total enhancements (open circle) are shown, as well as the chemical enhancement without T1PE (solid square) and T1PE without CE (open triangle). All measurements were performed with DMSO. Filtered spectrum is shown in FIG. 4. All enhancements shown here are relative, meaning no enhancement has a value of 1.0.

The experimentally measured results of the total enhancement are shown in FIG. 3 when THPC-AuNPs and AuNP@SiO$_2$ were mixed. FIG. 3 shows the measured fluorescent signals. As described in the Method section, if the signal is displayed in the unit $I_0$, which is the signal measured without any nanomaterials in water, then the signal has the same numerical values as enhancement. As a result, the vertical axis is labeled relative enhancement. The total enhancements (open circles) using X-rays with one Cu filter were higher than individual enhancements, which are also shown in FIG. 3. This filtration provided relatively high energy X-rays (spectrum shown in FIG. 4) and the dose rate of X-rays was 2.3 Gy/min measured with Fricke dosimetry without the presence of nanomaterials. The highest total enhancement is approximately 18 fold with 0.02 weight percent (wp) of gold in water in the form of THPC-AuNP and 7.5 wp AuNP@SiO$_2$. This is the highest total enhancement measured in this work.

The individual enhancement results are also shown in FIG. 3, which shows T1PE by AuNP@SiO$_2$ (open triangle) alone and CE with only THPC-AuNPs (solid square at zero AuNP@SiO$_2$ concentration). The measured $\epsilon_{T1PE}^r$ range from 1.0 fold (no enhancement) without AuNP@SiO$_2$ to 4.9 fold with 7.5 wp AuNP@SiO$_2$. $\epsilon_{CE0}^r$ with only 0.02 wp THPC-AuNPs and no AuNP@SiO$_2$ is 2.1 fold at this dose rate. Because CE is dependent of dose rate, adding AuNP@SiO$_2$ increases the dose rate and $\epsilon_{CE}^r$.[5] The absolute T1PE (defined as relative enhancement minus 1) ranges from 0.0 to 3.9 and absolute CE is 1.1 fold. This means that adding 0.02 wp THPC-AuNPs nearly doubled the 7-OH-CCA production, and adding 7.5 wp AuNP@SiO$_2$ to the aqueous solution increased the yield of 7-OH-CCA production by 3.9 fold. CE, T1PE, and total enhancement were measured in the presence of DMSO. There was no CE when only AuNP@SiO$_2$ were added because the surface of AuNPs is covered with silica, and there was no T1PE when only THPC-AuNPs are present because of the low weight percentage of the amount of THPC-AuNPs in water.

Figure 5A:
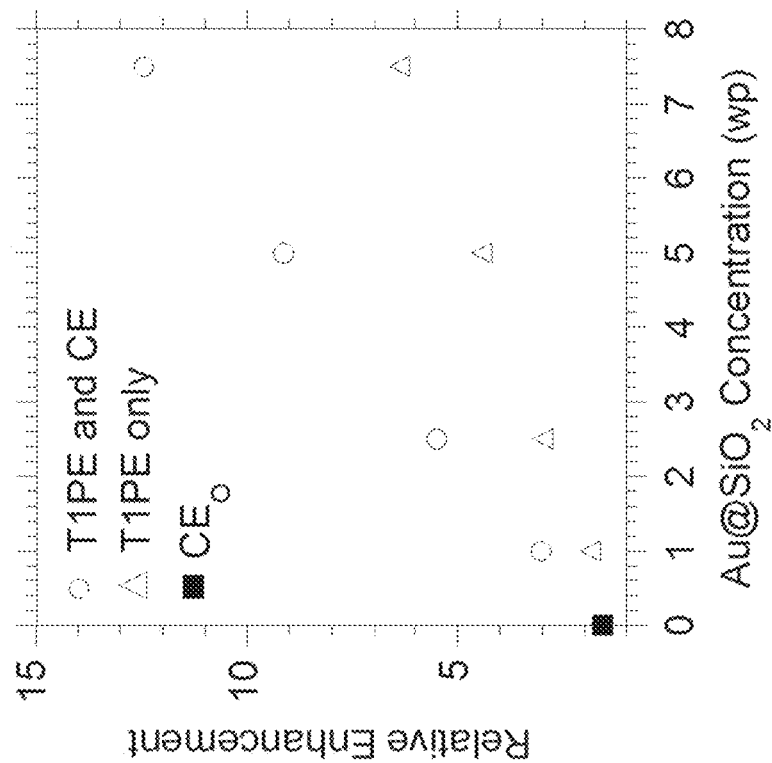
FIG. 5A illustrates the results of enhancement measurements using no filters.
Figure 5B:
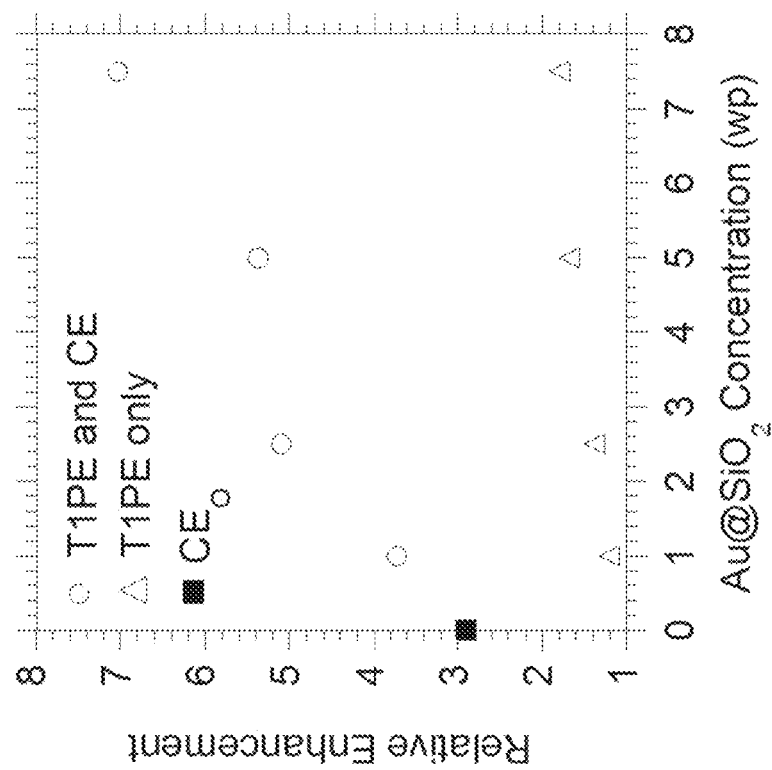
FIG. 5B illustrates the results of enhancement measurements using the double filter of one Cu and one Sn filter on the X-ray source. The total enhancements (open circle) are shown, as well as the chemical enhancement without T1PE (solid square) and T1PE without CE (open triangle). All measurements were performed with DMSO. Filtered spectrum is shown in FIG. 4 and FIG. 7. All enhancements shown here are relative, meaning no enhancement has a value of 1.0.
Figure 6:
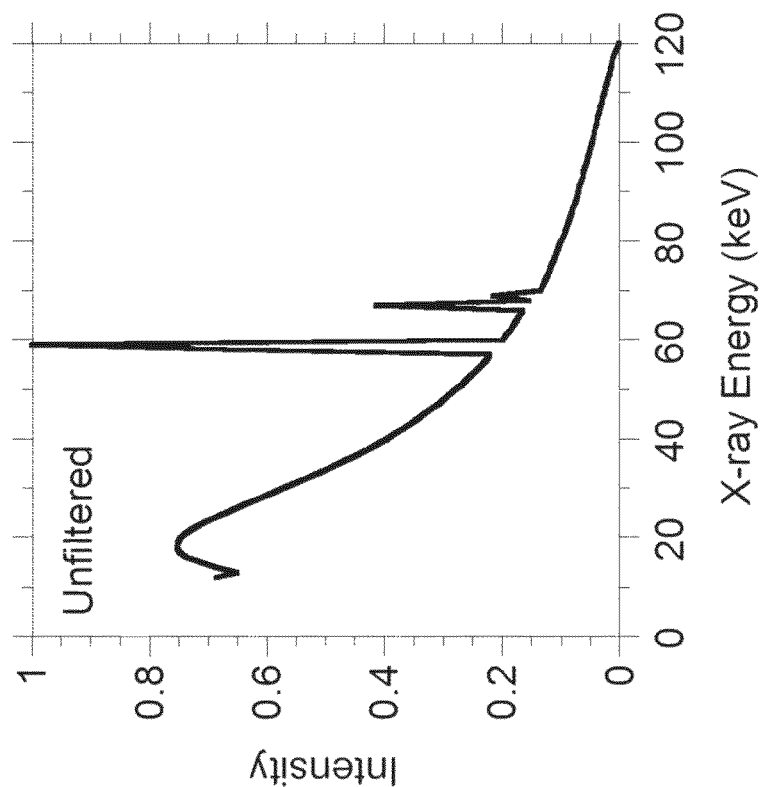
FIG. 6 illustrates the calculated X-ray spectrum without filters. Peak flux was normalized to the peak flux of the unfiltered spectrum.

Because CE is dose rate dependent, and dose rate depends not only the wattage of the X-ray but also the X-ray energy spectrum, CE hence depends on the X-ray energy spectrum as well. The wattage can be adjusted by the voltage or current or both for the source while the X-ray energy spectrum can be adjusted with filtration of the emitted X-ray spectrum. In addition to a single Cu filter, the enhancements without filters and with a double filter of Cu and Sn were also measured. FIG. 5A and FIG. 5B shows the enhancement results under these two conditions. FIG. 5A shows the results without filters. The dose rate was determined to be 16.5 Gy/min without AuNP@SiO$_2$. The X-ray spectrum is shown in FIG. 6. T1PE values $\epsilon_{T1PE}^r$ (open triangle) are lower, ranging from 1.0 (no AuNP@SiO$_2$) to 1.8 fold with 7.5 wp AuNP@SiO$_2$. This is nearly 3 times lower than one filter case. With only THPC-AuNPs, the net CE $\epsilon_{CE0}^r$ (solid square) is higher, at 2.9 fold. This was the highest CE measured in this work. This is because without filters, X-ray energies are much lower and can interact with water much more effectively, effectively resulting in lower T1PE but higher CE that relies on water generated radicals. The total enhancements for combined two nanomaterials were lower than those shown in FIG. 3. The highest total enhancement (open circle) for unfiltered X-rays is about 7.0 fold.

Figure 7:
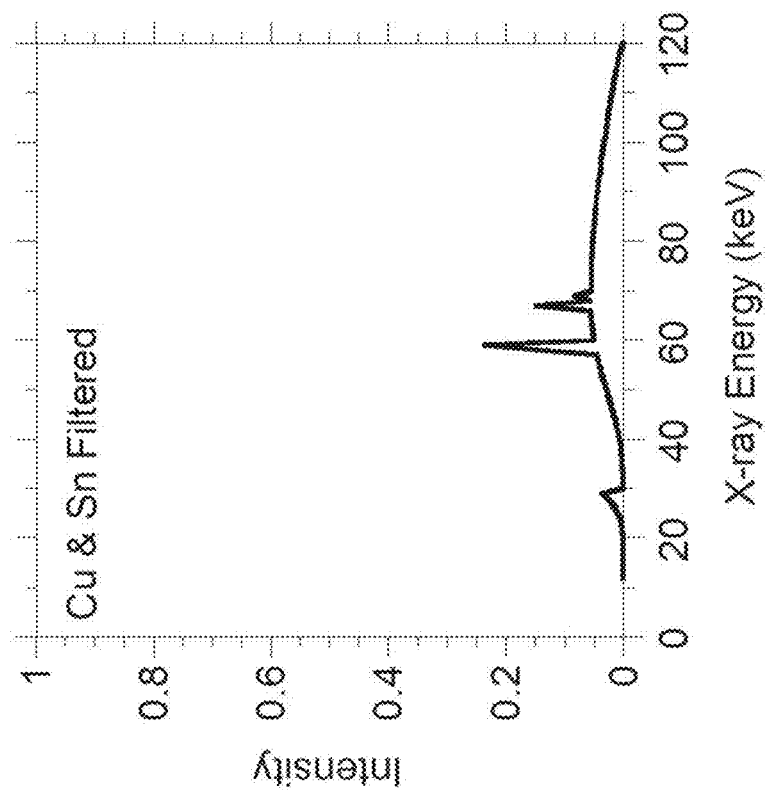
FIG. 7 illustrates the calculated X-ray spectrum filtered with a double filter of one Cu filter and one Sn filter. Peak flux was normalized to the peak flux of the unfiltered spectrum.

FIG. 5B shows the results obtained with the double filter of one Cu and one Sn. With this configuration, the X-ray dose rate at the sample was 0.82 Gy/min without AuNP@SiO$_2$. $\epsilon_{CE0}^r$ (solid square) is 1.5 and relative T1PE $\epsilon_{T1PE}^r$ (open triangle) ranges from 1.0 to 6.4 fold with 7.5 wp AuNP@SiO$_2$. This was the highest T1PE measured in this work and it shows that T1PE favors high energy X-rays. The X-ray spectrum is shown in FIG. 7. When THPC-AuNPs were mixed with AuNP@SiO$_2$, the total enhancements (open circle) are higher. The highest total enhancement is 12.5 fold.

The results shown above indicate that the highest total enhancement is achieved with moderately high dose rate and CE and T1PE using one Cu filter, not with either the highest CE or T1PE which were obtained with unfiltered X-rays and doubly filtered X-rays respectively. The descriptions of enhancement shown in FIG. 2 can be used to derive CE for the mixtures, which is not the same as the net CE $\epsilon_{CE0}^r$ without T1PE. If the experiment design is considered as adding AuNP@SiO$_2$ first and then THPC-AuNPs, then CE can be regarded as the enhancement by THPC-AuNPs to T1PE by AuNP@SiO$_2$. The other way around of using T1PE to enhancement CE is to use to derive the total enhancement algorithm, although this was not performed because it is conceptually less clear. When there is no THPC-AuNPs but just AuNP@SiO$_2$, there is only T1PE and the enhancement is described as:

$$\epsilon^r_{T1PE} = \frac{I_{T1PE}}{I_0} \quad (1)$$

Adding THPC-AuNPs into the AuNP@SiO$_2$ solution creates CE on top of T1PE, and we can arrive at the following equation according to the description of CE shown in FIG. 2:

$$\epsilon^r_{CE} = \frac{I_{Total}}{I_{T1PE}}, \quad (2)$$

for the total signal and the signal without CE, which is the T1PE signal. As shown in Eq. (1), at a specific AuNP@SiO$_2$ concentration there is an enhancement (T1PE) associated with it. Adding AuNP@SiO$_2$ is therefore equivalent to increasing the dose rate and hence the total dose by the T1PE enhancement factor, which is $\epsilon^r_{T1PE}$. If $I_0$ is chosen as the unit for the measured signal, then numerically $\epsilon^r_{T1PE} = I_{T1PE}$.

Although the 3-CCA dosimetric reaction itself or many other reactions are neither dose nor dose rate dependent, when 3-CCA assay is used with THPC-AuNPs there is CE even without AuNP@SiO$_2$, which can also be expressed by Eq. (2) if $I_{T1PE} = I_0$. By definition, the combined enhancement generates the total enhancement signal:

$$I_{Total} = I_0 \epsilon^r_{Total} \quad (3)$$

Using Eqs. (1) and (2), the total enhancement signal is also:

$$I_{Total} = \epsilon^r_{CE} I_{T1PE} = \epsilon^r_{CE} \epsilon^r_{T1PE} I_0 \quad (4)$$

Combining Eq. (3) and (4):

$$\epsilon^r_{CE} \epsilon^r_{T1PE} I_0 = I_0 \epsilon^r_{Total} \quad (5)$$

Eliminating $I_0$ on both sides of the equation arrives at:

$$\epsilon^r_{Total} = \epsilon^r_{T1PE} \epsilon^r_{CE} \quad (6)$$

This equation explains how the total enhancement is related to the individual physical and chemical enhancements. Eq. (6) can be used to (i) predict the total enhancement if T1PE and CE are known experimentally, (ii) derive T1PE or CE if the total enhancement and one of the two individual enhancements are known, and (iii) to verify the validity of the algorithm when all three are known.

Figure 8:
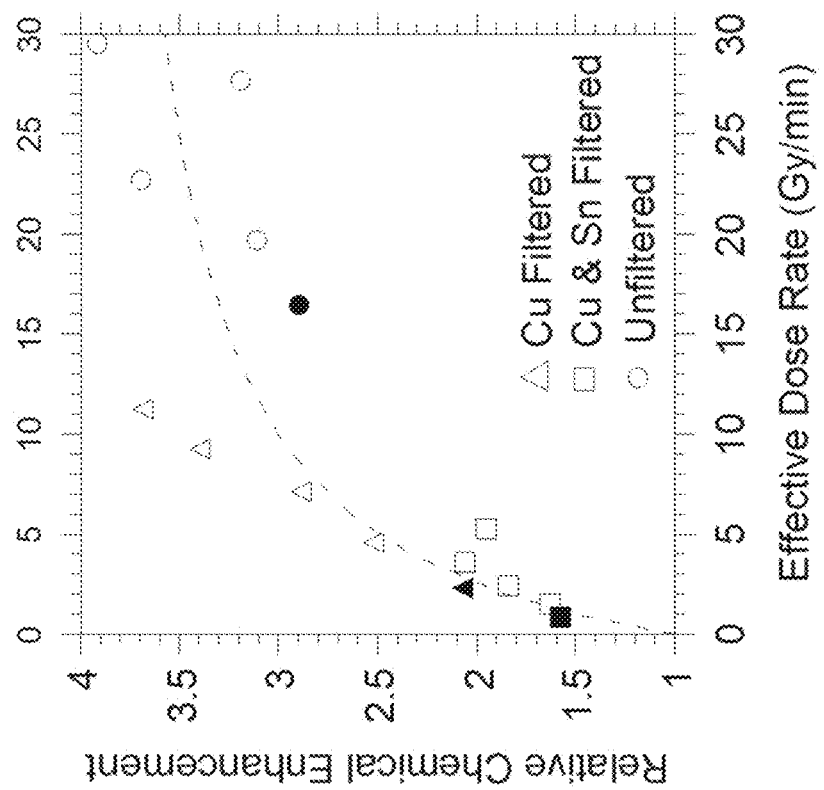
FIG. 8 illustrates the measured net CE (solid symbols) $\epsilon_{CE0}^R$ and calculated CE $\epsilon_{CE}^r$ (open symbols) as a function of dose rate in all three cases shown in FIG. 3 and FIG. 5A-FIG. 5B. The dose rates were cross calibrated with Fricke dosimetry. The dashed line is for visual guidance using $$a \frac{a*x}{b+x} + 1 \text{ formula,}$$

All three functions can be demonstrated here. Using Eq. (2), the corresponding $\epsilon^r_{CE}$ embedded in FIG. 3 and FIG. 5A-FIG. 5B can be calculated and the values are displayed in FIG. 8 (open symbols). Also shown in FIG. 8 are the measured net CE $\epsilon^r_{CE0}$ (solid symbols) at three absolute dose rates calibrated with Fricke dosimetry. The three measured $\epsilon^r_{CE0}$ values shown in FIG. 8 follow the general trend of the rest of CE, confirming the validity of the algorithm. These three CE values and the T1PE values shown in FIG. 3 and FIG. 5A-FIG. 5B can be used to predict the total enhancements under those conditions.

$\epsilon^r_{CE}$ shown in FIG. 8 increases linearly at low dose rates (<3 Gy/min) and saturates at high dose rates (>3 Gy/min), e.g., in the unfiltered cases. This is lower than the value of 20 Gy/min given in an early report in which it was found that CE using 3-CCA as the probe may increase (not linearly though) up to dose rate of 20 Gy/min and saturate between 20 and 40 Gy/min using PEG-AuNPs.

It should be noted that all the T1PE values without CE and the CE values without T1PE shown above are obtained experimentally, whether CE saturates or T1PE follows the same profile as a function of concentration of AuNP@SiO$_2$. Without wishing to be bound by theory, it is not believed that T1PE will change when CE is present due to the physical nature of T1PE. However, because CE is dose rate dependent, CE values in the presence of T1PE will be different from the ones without T1PE. A special case is given below in which one may predict the total enhancement using T1PE and the net CE values, e.g., CE without T1PE.

When CE is under a non-saturation condition, Eq. (6) can be further developed conceptually. It is shown in this work that dose rate D can be adjusted by changing the X-ray source such as adding filters or be changed by adding AuNP@SiO$_2$. For a specific source setting without AuNP@SiO$_2$, the dose rate is described as $D_0$. Adding THPC-AuNPs does not change $D_0$ because their T1PE influence is negligible. Adding AuNP@SiO$_2$ causes T1PE to increase, which effectively increases dose rate. The results shown in FIG. 3 and FIG. 5A-FIG. 5B as well as previously published results both indicate that adding AuNP@SiO$_2$ to water can increase the effective dose rate by many fold.[7] The dose rate with AuNP@SiO$_2$ added can be expressed, assuming a linear relationship:

$$D = \epsilon^r_{T1PE} D_0 \quad (7)$$

Because dose rate is measured with a specific probe reaction, which is 3-CCA to 7-OH-CCA conversion in this Example, the addition of nanomaterials THPC-AuNPs and AuNP@SiO$_2$ can cause CE and T1PE and the total enhancement can be greater than either of them individually. From FIG. 8, if CE is linearly proportional to dose rate (before saturation (<3 Gy or possibly lower), which may not be true for all cases as shown in FIG. 8), then at a certain dose rate D, CE becomes:

$$\epsilon^r_{CE} = 1 + \epsilon^a_{CE0} \frac{D}{D_0} = 1 + (\epsilon^r_{CE0} - 1)\frac{D}{D_0} = 1 + (\epsilon^r_{CE0} - 1)\epsilon^r_{T1PE} \quad (8)$$

This is because only the absolute CE part is enhanced further by the dose rate, and Eq. (6) becomes:

$$\epsilon^r_{Total} = \epsilon^r_{T1PE} \epsilon^r_{CE} = \epsilon^r_{T1PE}(1 + (\epsilon^r_{CE0} - 1)\epsilon^r_{T1PE}) \quad (9)$$

The benefit of using this equation is that it is possible to calculate the total enhancement using the experimentally measured $\epsilon^r_{CE0}$ and $\epsilon^r_{T1PE}$ if there is no dose rate saturation for CE. In practice, as shown in FIG. 8, CE saturates at about 3 Gy/min. As a result, one can use Eq. (9) to predict total enhancement before mixing the T1PE and CE nanoparticles. The experimentally obtained total enhancement begins to deviate from Eq. (9) above 3.0 Gy/min and only Eq. (6) will have to be used to retrieve CE values.

As mentioned above, the experimental results shown in FIG. 3, FIG. 5A-FIG. 5B, and FIG. 8 were measured using rate equations in a report published earlier.[5] In order to fit all three sets of data, the rate constant responsible for chemical enhancement was adjusted. In the fitting, experimentally obtained T1PE were used to modify the Fricke calibrated dose rates. The fitting results are shown in FIG. 9, which shows a generally good agreement between the simulated and experimental results. Because T1PE is approximately linearly proportional to concentration, the data shown in FIG. 9 can also be viewed as how the total enhancement depends on T1PE as well. The match between the experimental and fitted results demonstrates the validity of using CE and T1PE to account for the total enhancement, which is expressed as the multiplication of the two.

Discussion

The results presented here reveal the multiplication algorithm for combined chemical and type 1 physical enhancement. There are several advantages to use this combined enhancement methodology. First, a much higher overall enhancement may be achieved and the algorithm may apply to many other reactions. For instance, aniline polymerization occurring on the surface of silver core—gold shell nanostructures has a chemical enhancement of 30 fold.[6] It is not known if the polymerization reaction obeys exactly the same saturation process as the 3-CCA reaction. If that reaction is mixed with other types of physical enhancements such as the type 2 physical enhancement that can be as high as 200 fold, then it is possible to obtain a very high total enhancement value if the multiplication algorithm holds.

Another benefit is that it is possible to reach an enhancement that otherwise is difficult for either individual enhancement mechanism. For example, the highest Au concentration that we use here is about 7.5 wp using AuNP@SiO$_2$ and the highest enhancement is about 5.0 fold.[7] Although up to 15 wp AuNP@SiO$_2$ solution can be prepared, it is nearly impossible to reach 15 fold enhancement with this nanomaterial alone. With the assistance of CE from only 0.02 wp THPC-AuNPs, the total enhancement with the same amount of AuNP@SiO$_2$ can generate 18 fold total enhancement.

The third advantage is that much fewer nanomaterials are needed for the combined individual enhancements than individual enhancements. For example, if a 10-fold enhancement is desired, then it is possible to use 4 wp AuNP@SiO$_2$ and 0.02 wp THPC-AuNPs to generate such a total enhancement. On the other hand, one would need nearly 12 wp AuNP@SiO$_2$ to obtain a 10-fold T1PE if linearly extrapolation can be done based on FIG. 5B.

Because T1PE is an average enhancement, it is not confined to the surface region of nanomaterials that cause the enhancement. As a result, it is possible to generate T1PE microns away from the T1PE causing nanomaterials. This allows the multiplication of T1PE and CE to occur at a remote location from T1PE providing nanomaterials. Because CE involves the use of the surface of nanomaterials, CE nanoparticles have to be delivered to the target. For example, it is possible to arrange a number of large AuNPs outside the target volume and to deliver a small amount of CE nanomaterials in the target volume, such as the cell nucleus. It is possible for the cell to take up a large quantity of large nanoparticles in the cytoplasm to create a relatively high T1PE in the nearby nucleus. Then it is possible to deliver a small quantity of small nanoparticles into the nucleus to cause CE, which could occur as shown in an earlier report. The combination creates a much higher total enhancement of damage to the cell under irradiation, and the overall enhancement in the target volume, for example the nucleus, can be much higher than either enhancement.

Another way to maximize the total enhancement is to use different X-ray energy spectra to generate T1PE and CE. For example, if low energy X-rays in the range of 10-30 keV to generate high CE and high energy X-rays in the region of 40-100 keV to generate high T1PE are used, then it is possible to maximize CE and T1PE and therefore obtain a much higher total enhancement. For much higher energy photons such as gamma rays, the combined enhancement will be very similar to individual ones due to the unknown CE and low PE generated from nanomaterials. The results shown here therefore indicate the importance of using keV X-rays for enhancement purposes.

Of note is that as long as the two nanomaterials do not interfere destructively with each other when the two nanoparticles are mixed together, which is the case here, then T1PE and CE can co-exist and the overall enhancement follows the multiplicity algorithm described here. However, if the two types of NPs cause each other to precipitate or aggregate when 3-CCA or DMSO is added, then the combined enhancement may be lower.

It is possible to experimentally measure all the CE values if a much more powerful X-ray is available. Currently the dose rate accomplished by adding AuNP@SiO$_2$ using filtered X-rays cannot be reproduced using the X-ray source alone. For example, in the one filter case the highest dose rate was achieved with the largest amount of 7.0 wp of AuNP@SiO$_2$. This dose rate with the same X-ray spectrum cannot be obtained with the X-ray source alone, so CE at this dose rate cannot be measured without using AuNP@SiO$_2$. Only three data points in FIG. 8 are experimentally measured without AuNP@SiO$_2$ and the rest are derived using Eq. (6).

Eq. (9) may be simplified if both $\epsilon_{CE0}^r$ and $\epsilon_{T1PE}^r$ are low. In this case, which may happen to samples irradiated by MeV γ-rays, there is little CE and the total enhancement is the same as T1PE. For the simulated results shown in FIG. 9, the fitted data show the least degree of saturation for the lowest dose rate case (double filter) and strongest saturation at the highest dose rate case (no filters). The simulation results confirm that the combined total enhancement can be satisfactorily explained by the interplay between physical and chemical enhancement, which fit in a multiplication algorithm to give rise to the total enhancement.

Conclusions

The experimentally obtained total enhancement $\epsilon_{Total}^r$ was shown to follow a multiplication algorithm $\epsilon_{Total}^r = \epsilon_{T1PE}^r \epsilon_{CE}^r$ of the two non-interfering individual enhancements of type 1 physical enhancement $\epsilon_{T1PE}^r$ and chemical enhancement $\epsilon_{CE}^r$. All enhancements were relative enhancements, meaning that the enhancement values are 1.0 when there is no enhancement. The multiplication algorithm can be directly derived from the definition of these enhancements. Chemical enhancement was found to begin to saturate at 3.0 Gy/min. No clear saturation was observed with type 1 physical enhancement at up to 30 Gy/min as a function of AuNP@SiO$_2$ concentration. Simulation results obtained using rate equations for predicting chemical enhancement agreed with the experimentally observed total enhancements and hence confirm the validity of the algorithm that governs the total enhancement, type 1 physical enhancement and chemical enhancement. A graphical depiction of total enhancement is presented in FIG. 10.

Further Discussion

Enhancements to X-ray effects by nanomaterials have been discovered and there are many basic enhancement processes. However, combining these basic enhancements is not straightforward and, prior to the present disclosure, there has been no such combination demonstrated experimentally or theoretically. It is foreseeable that there are many ways to combine them and some of which may not yield further enhancement than the individual enhancements unless the individual enhancements are properly combined.

Here Applicants have shown examples of how to properly utilize individual enhancements such as type 1 physical enhancement (T1PE) and chemical enhancement (CE) to create the highest possible total enhancement. The individual enhancements can be controlled by adjusting the operation of the X-ray source such as either changing the wattage of the X-ray source or adding X-ray filters to tune the X-ray spectrum. One can also change the quantity, size and surface coating of the nanomaterials to change the effective dose rate. Furthermore, it is possible to control the location of T1PE and CE so that CE exists in a volume or region where there are no nanoparticles that cause T1PE because T1PE can extend to a remote region many micrometers away from these T1PE nanoparticles, as far as 10 microns or greater distance. There must be CE nanoparticles in the region though because CE requires the surface of CE nanoparticles. Chemical enhancement may occur within 10 nm to 1,000 nm of the target, whereas type 1 physical enhancement may occur within microns or even tens of microns of the target. Nanomaterials for chemical enhancement may be placed 1 nm to 10 nm away from the target, and the type 1 physical enhancement nanomaterials may be placed, for example, tens of nanometers away from the target, or 1 μm to about 10 μm away from the target. One example of application is to deliver small, nuclear-penetrating gold nanoparticles (size smaller than 10 nm in diameter) so that they can cause chemical enhancement to DNA strand breaks while delivering large gold nanoparticles (10 to 1000 nm in diameter) to the cell outside the nuclei to cause significant T1PE. Together the total enhancement to nuclear DNA strand breaks can be much greater than the two individual enhancements. It is also possible to employ 100 keV X-rays from one source to generate T1PE efficiently and 10-30 keV X-rays from another source to generate CE efficiently. For example, in cancer therapy the 100 keV X-ray source can be a source located outside the body and the low energy X-ray source can be a catheter planted near the cancer site. Both sources may deliver low doses of X-rays.

In the example shown here, Applicants demonstrated net CE (CE0) of 1 to 3 fold without T1PE nanoparticles, and T1PE 1 to 7 fold with CE nanoparticles. All enhancements are relative enhancements, meaning the enhancement is 1.0 fold when there is no enhancement compared with just water, without any nanomaterial. Applicants showed that the total enhancement follows a multiplication algorithm, so that maximum total enhancement occurs when the two individual enhancements are moderately high and neither is too low. In this case, the total enhancement can reach 18 fold when T1PE is 5.0 fold and initial CE0 is 2.0 fold. The actual CE is 3.5 fold when T1PE is considered. Such an enhancement is not achievable with either individual enhancement.

REFERENCES

1. Guo, T., *Nanoparticle Enhanced X-Ray Therapy*, in *ACS Annual Meeting* 2004: Philadelphia, Pa.
2. Hainfeld, J., D. Slatkin, and H. Smilowitz, The use of gold nanoparticles to enhance radiotherapy in mice. *Phys. Med. Bio.*, 2004. 49, N309-N315.
3. Foley, E., J. Carter, F. Shan, and T. Guo, Enhanced relaxation of nanoparticle-bound supercoiled DNA in X-ray radiation. *Chem. Commun.*, 2005, 3192-3194.
4. Carter, J. D., N. N. Cheng, Y. Q. Qu, G. D. Suarez, and T. Guo, Nanoscale energy deposition by x-ray absorbing nanostructures. *J. Phys. Chem. B*, 2007. 111, 11622-11625.
5. Cheng, N. N., Z. Starkewolf, A. R. Davidson, A. Sharmah, C. Lee, J. Lien, and T. Guo, Chemical Enhancement by Nanomaterials under X-ray Irradiation. *J. Am. Chem. Soc. Commun.*, 2012. 134, 1950-1953.
6. Davidson, R. A. and T. Guo, An Example of X-ray Nanochemistry: SERS Investigation of Polymerization Enhanced by Nanostructures under X-ray Irradiation. *Journal of Physical Chemistry Letters*, 2012. 3, 3271-3275.
7. Davidson, R.A. and T. Guo, Average Physical Enhancement by Nanomaterials under X-ray Irradiation. *Journal of Physical Chemistry C*, 2014. 118, 30221-30228.
8. Lee, C., N. N. Cheng, R. A. Davidson, and T. Guo, Geometry Enhancement of Nanoscale Energy Deposition by X-rays. *J. Phys. Chem. C*, 2012. 116, 11292-11297.
9. Ionita, P., F. Spafiu, and C. Ghica, Dual behavior of gold nanoparticles, as generators and scavengers for free radicals. *Journal of Materials Science*, 2008. 43, 6571-6574.
10. Perrault, S. D. and W. C. W. Chan, Synthesis and Surface Modification of Highly Monodispersed, Spherical Gold Nanoparticles of 50-200 nm. *Journal of the American Chemical Society*, 2009. 131, 17042-17043.
11. Plech, A., J. Kimling, M. Maier, B. Okenve, V. Kotaidis, and H. Ballot, Turkevich method for gold nanoparticle synthesis revisited. *Journal of Physical Chemistry B*, 2006. 110, 15700-15707.
12. Duff, D., A. Baiker, I. Gameson, and P. Edwards, A New Hydrosol of Gold Clusters .2. A Comparison of Some Different Measurement Techniques. *Langmuir*, 1993. 9, 2310-2317.
13. Olzzanski, A., N. V. Klassen, C. K. Ross, and K. R. Shorn, *The IRS Fricke Dosimetry System*, 2002.
14. Cheng, N. N., Z. Starkewolf, A. R. Davidson, A. Sharmah, C. Lee, J. Lien, and T. Guo, Chemical Enhancement by Nanomaterials under X-ray Irradiation. *J. Am. Chem. Soc. Commun.*, 2012. 134, 1950-1953.

What is claimed is:

1. A method of enhancing a chemical reaction, the method comprising:
    a) providing a sample comprising:
        (1) a first population of nanomaterials comprising (i) an active metal surface, and
        (ii) a diameter in the range of 1 nm to 10 nm;
        (2) a second population of nanomaterials comprising a diameter in the range of 10 nm to 1,000 nm;
        (3) one or more chemical reactants; and,
    b) irradiating the sample with irradiation energy for a period of time sufficient for the one or more chemical reactants to undergo a chemical reaction to yield one or more products, wherein the irradiation energy is filtered, wherein the chemical reaction occurs at a reaction rate that is increased as compared to a corresponding control sample, and wherein the irradiation energy comprises X-rays.

2. The method of claim 1, wherein the sample comprises water.

3. The method of claim 1, wherein the first population of nanomaterials comprises nanoparticles.

4. The method of claim 3, wherein the nanoparticles comprise gold (Au).

5. The method of claim 1, wherein the second population of nanomaterials comprise a ligand comprising tetrakis (hydroxymethyl) phosphonium chloride (THPC) or PEG.

6. The method of claim 1, wherein the first population of nanomaterials is present in the sample at a concentration in the range of 0.001 to 0.1 weight percent first population of nanomaterials in the sample.

7. The method of claim 1, wherein the first population of nanomaterials comprise a diameter in the range of 1 nm to 5 nm.

8. The method of claim 1, wherein the first population of nanomaterials are present 1 nm to 10 nm away from the one or more chemical reactants.

9. The method of claim 1, wherein the second population of nanomaterials comprises nanoparticles.

10. The method of claim 9, wherein the nanoparticles comprise gold (Au).

11. The method of claim 1, wherein the second population of nanomaterials comprise a ligand comprising silica.

12. The method of claim 1 wherein the second population of nanomaterials is present in the sample at a concentration in the range of 0.1 to 10 weight percent second population of nanomaterials in the sample.

13. The method of claim 1, wherein the second population of nanomaterials comprises a diameter in the range of 10 nm to 200 nm.

14. The method of claim 1, wherein the second population of nanomaterials are present 0.1 µm to 10 µm away from the one or more chemical reactants.

15. The method of claim 1, wherein the second population of nanomaterials comprises an inert surface.

16. The method of claim 1, wherein the irradiation energy is at a dose rate in the range of 0.1 Gy/min to 100 Gy/min.

17. The method of claim 1, wherein the irradiation energy comes from multiple sources.

18. The method of claim 1, wherein the corresponding control sample is a sample which does not comprise the first population of nanomaterials and/or the second population of nanomaterials.

19. A nanomaterial mixture comprising:
a first population of nanomaterials, wherein the first population of nanomaterials are characterized by (i) an active metal surface, and (ii) a diameter in the range of 1 nm to 10 nm;
a second population of nanomaterials, wherein the second population of nanomaterials comprises nanoparticles, wherein the nanoparticles comprise gold (Au), and wherein the second population of nanomaterials are characterized by a diameter in the range of 10 nm to 1,000 nm; and
one or more chemical reactants, wherein the first population of nanomaterials and the second population of nanomaterials of the nanomaterial mixture are configured to cause the chemical reactants to undergo a chemical reaction to yield one or more products when irradiated with irradiation energy for a period of time, wherein the chemical reaction occurs at a reaction rate that is increased as compared to a corresponding control sample, and wherein the second population of nanomaterials are present 0.1 µm to 10 µm away from the one or more chemical reactants.

20. The nanomaterial mixture of claim 19, wherein the first population of nanomaterials is present in the nanomaterial mixture at a concentration in the range of 0.01 to 0.1 weight percent first population of nanomaterials in the nanomaterial mixture.

21. The nanomaterial mixture of claim 19, wherein the second population of nanomaterials is present in the nanomaterial mixture at a concentration in the range of 1 to 10 weight percent second population of nanomaterials in the nanomaterial mixture.

22. The nanomaterial mixture of claim 19, wherein the irradiation energy is up to 3.0 Gy/min.

23. The nanomaterial mixture of claim 19, wherein the nanomaterial mixture causes at least an 18 fold increase in the deposition of energy from the irradiation energy when compared to the deposition of energy from the irradiation energy in the corresponding control sample.

* * * * *